United States Patent [19]
Goodman et al.

[11] Patent Number: 5,547,859
[45] Date of Patent: Aug. 20, 1996

[54] CHAIN-TERMINATING NUCLEOTIDES FOR DNA SEQUENCING METHODS

[76] Inventors: Myron F. Goodman, 4719 Alminar Ave., LaCanada, Calif. 91011; Linda J. Reha-Krantz, 10044 87th Avenue, Edmonton, Alberta, Canada, T6E 2N9

[21] Appl. No.: 101,593

[22] Filed: Aug. 2, 1993

[51] Int. Cl.$^6$ ..................................................... C12P 19/34
[52] U.S. Cl. .................. 435/91.1; 435/91.2; 536/27.14; 536/28.2
[58] Field of Search ............................ 435/6, 91.2, 91.1; 935/78; 536/27.14, 28.2

[56] References Cited

U.S. PATENT DOCUMENTS

| | | | |
|---|---|---|---|
| 4,666,892 | 5/1987 | Fox et al. | 514/49 |
| 4,935,361 | 6/1990 | Lin et al. | 435/172.3 |
| 4,962,020 | 10/1990 | Tabor et al. | 435/6 |

FOREIGN PATENT DOCUMENTS

| | | |
|---|---|---|
| 0252683 | of 0000 | European Pat. Off. . |
| 0516245 | of 0000 | European Pat. Off. . |
| 0309969 | of 0000 | European Pat. Off. . |
| 3546374 | of 0000 | Germany . |
| 4214112 | of 0000 | Germany . |
| WO9106679 | of 0000 | WIPO . |
| WO9405684 | of 0000 | WIPO . |
| WOA9116446 | of 0000 | WIPO . |

OTHER PUBLICATIONS

Chidgeavadze et al., Biochimica et Biophysica Acta 868: 145–152 (1986).
Bernad et al. "A Conserved 3'-5' Econuclease Active Site in Prokaryotic and Eukaryotic DNA Polymerases" *Cell*, vol. 59, 219–228, (1989).
Ito et al. "Compilation and alignment of DNA polymerase sequences" *Nucleic Acids Research*, vol. 19, No. 15, 4045–4047.
Bonner, C. A., Hays, S., McEntee, K. and Goodman, M. F.; "DNA Polymerase II Is Encoded By The DNA Damage–Inducible dinA Gene of *Escherichia coli*"; *Proc. Natl. Acad. Sci. USA*, vol. 87, 7663–7667 (Oct. 1990).
Braithwaite, D. K. and Ito, J.; "Compilation, Alignment, and Phylogenetic Relationships Of DNA Polymerases"; *Nuc. Acids Res.*, vol. 21, No. 4, 787–802 (1993).
Kunkel, T. A., Roberts, J. D. and Zakour, R. A., "Rapid and Efficient Site–Specific Mutagenesis Without Phenotypic Selection"; *Method. Enz.*, vol. 154, 367–382 (1987).
Lin, T–C., Rush, J., Spicer, E. K. and Konigsberg, W. H., "Cloning and Expression of T4 DNA Polymerasse"; *Proc. Natl. Acad. Sci. USA*, vol. 84, 7000–7004 (Oct. 1987).
McPheeters, D. S., Christensen, A., Young, E. T., Stormo, G. and Gold L.; "Translational Regulation Of Expression Of The Bacteriophage T4 Lysozyme Gene"; *Nuc. Acids Res.*, vol. 14, No. 14 5813–5826 (1986).
Rhea–Krantz, L. J.; "Amino Acid Changes Coded By Bacteriophage T4 DNA Polymerase Mutator Mutants Relating Structure to Function"; *J. Mol. Biol.*, vol. 202, 711–724 (1988).
Rhea–Krantz, L. J.; "Genetic Dissection of T4 DNA Polymerase Structure–Function Relationships"; *The Molecular Biology of Bacteriophage T4*, J. Karam (ed.), American Society for Microbiology, Washington, D.C. (in press).
Sanger, F., Nicklen, S. and Coulson, A. R.; "DNA Sequencing With Chain–Terminating Inhibitors"; *Proc. Natl. Acad. Sci. USA*, vol. 74, No. 12, 5463–5467 (Dec. 1977).
Tabor, S. and Richardson, C. C.; "DNA Sequence Analysis With A Modified Bacteriophage T7 DNA Polymerase"; *J. Biol. Chem.*, vol. 265, No. 14, 8322–8328 (May 15, 1990).
Wurgler, S. M. and Richardson, C. C.; "Structure And Regulation Of The Gene For dGTP Triphosphohydrolase From *Escherichia coli*"; *Proc. Natl. Acad. Sci. USA*, vol. 87, 2740–2744 Apr. 1990).

*Primary Examiner*—W. Gary Jones
*Assistant Examiner*—Scott Houtteman
*Attorney, Agent, or Firm*—Robbins, Berliner & Carson

[57] ABSTRACT

There are provided variant family B DNA polymerases having no 3'→5' exonuclease activity. These variant polymerases have utility as DNA sequencing polymerases. Methods for DNA sequencing with family B DNA polymerases and chain-terminating nucleotides not previously used for sequencing have been developed. The methods disclosed involve the use of family B DNA polymerases not known heretofore to have utility in DNA sequencing, such as variant or wild type forms of phage T4 DNA polymerase or *Escherichia coli* DNA polymerase II, with novel combinations of deoxynucleotides and chain-terminating nucleotides.

6 Claims, 6 Drawing Sheets

NUCLEOTIDE STRUCTURES

2'-DEOXYRIBONUCLEOSIDE TRIPHOSPHATES (dNTPs)

dTTP  dCTP  dATP  dGTP

2',3'-DIDEOXYRIBONUCLEOSIDE TRIPHOSPHATES (ddNTPs)

B=Thy
B=Cyt
B=Gua
B=Ade

3'-AMINO-2',3' DIDEOXYRIBONUCLEOSIDE TRIPHOSPHATES (3'-NH$_2$ ddNTPs)

B=Thy
B=Cyt
B=Gua
B=Ade

ARABINONUCLEOSIDE TRIPHOSPHATES (araNTPs)

B=Ura
B=Cyt

Ura=

5,547,859

1

CHAIN-TERMINATING NUCLEOTIDES FOR DNA SEQUENCING METHODS

BACKGROUND OF THE INVENTION

The present invention relates to modifications of the DNA sequencing method developed by F. Sanger (Sanger, F., Nicklen, S., Coulson, A. R. (1977) *Proc. Natl. Acac. Sci. U.S.A.* 74, 5463–5467) as well as to novel enzymes which can be used for DNA sequencing. The Sanger sequencing method is based on in vitro DNA synthesis reactions in the presence of a primed DNA template, 2'-deoxyribonucleoside triphosphates (dNTPs, see FIG. 1), and 2',3'-dideoxyribonucleoside triphosphates (ddNTPs, FIG. 1). The latter, when incorporated by a DNA polymerase into a polynucleotide chain, terminate further chain elongation. The DNA products are thus a series of polynucleotide chains complementary to the template and terminated with specific dideoxynucleotides. The DNA sequencing products can be separated by size and the pattern of the products gives the DNA sequence.

In principle, DNA polymerases from a variety of organisms and a variety of chain-terminating nucleotides should be useful to sequence DNA. In practice, few DNA polymerases and chain-terminating nucleotides have been found to be suitable for this purpose. As an example of a DNA sequencing polymerase, the development of bacteriophage T7 DNA polymerase, Sequenace™, will be reviewed (Tabor, S., and Richardson, C. C. (1990) *J. Biol. Chem.* 265, 8322–8328). In order to obtain an unambiguous DNA sequence it is necessary that the majority of sequencing products terminate with a dideoxynucleotide and that all the sequencing products are represented equally. Two phage T7 DNA polymerase activities degrade DNA sequencing products and, thus, these activities must be eliminated in order to prevent degradation of dideoxynucleotide-terminated sequencing products. One activity, 3'→5'-exonuclease activity, was removed by constructing an exonuclease deficient variant of T7 DNA polymerase. T7 DNA polymerase also has pyrophosphorolytic activity which can degrade the sequencing products. Pyrophosphatase was added to degrade pyrophosphate produced in the DNA sequencing reactions; without pyrophosphate, there is no pyrophosphorolysis. A further refinement of the sequencing reactions was to use $Mn^{2+}$ in place of $Mg^{2+}$ which resulted in a more equal distribution of reaction products. Although this brief review of the development of T7 DNA polymerase into a sequencing polymerase is a simplification, the review illustrates the point that modification of a natural DNA polymerase as well as development of reaction conditions is required in order to obtain high quality DNA sequence information using the chain-terminating sequencing method.

Optimal DNA sequencing conditions using the chain-terminating method have not yet been achieved. Ambiguous sequencing information is still observed which necessitates determining the DNA sequence of both DNA strands. Also, the use of $Mn^{2+}$ in place of $Mg^{2+}$ increases the amount of DNA template required for sequencing reactions. Thus it would be advantageous to develop novel methods that would improve or complement existing sequencing procedures.

The wild type T4 DNA polymerase gene has been cloned and the protein product expressed (Lin, T.-C., Rush, J. R., Spicer, E. K., and Konigsberg, W. H. (1987) *Proc. Natl. Acad. Sci. U.S.A.* 84, 7000–7004; U.S. Pat. No. 4,935,361 to Lin et al.) and *E. coli* DNA polymerase II has been cloned

2 and expressed (Bonner, C. A., Hays, S., McEntee, K., and Goodman, M. F. (1990) *Proc. Natl. Acad. Sci. U.S.A.* 87, 7663–7667). Standard oligonucleotide-directed mutagenesis techniques have been used to construct novel forms of T4 DNA polymerase and *E. coli* DNA polymerase II. Thus, the means exist to economically prepare large quantities of wild type and variant T4 DNA polymerase and *E. coli* DNA polymerase II.

Another aspect of the invention is to use genetic analysis to identify DNA polymerases with properties useful for DNA sequencing. T4 DNA polymerase is one of the most extensively genetically characterized DNA polymerases (Reha-Krantz, L. J. (1993) *In Molecular Biology of Bacteriophage* T4, ed. Karam J., American Association for Microbiology, in press); hence, some mutant DNA polymerases already identified may have properties useful for DNA sequencing and new mutants can be isolated directly. A method to isolate novel T4 DNA polymerases with useful DNA sequencing properties would be of additional utility.

SUMMARY OF THE INVENTION

In accordance with aspect of the invention, there are provided novel enzymes which may be used as DNA sequencing polymerases. These enzymes result from genetic mutations of family B DNA polymerases. These mutations eliminate the 3'→5' exonuclease activity of these novel family B DNA polymerases.

In accordance with another aspect of the invention, there are provided methods that enable phage T4 DNA polymerase and *E. coli* DNA polymerase II to be used as DNA sequencing polymerases. DNA polymerase modifications that convert phage T4 DNA polymerase and *E. coli* DNA polymerase II into DNA sequencing polymerases can also be used to similarly modify DNA polymerases having protein sequence homology with these two polymerases. DNA polymerases with protein sequence similarities to T4 DNA polymerase and *E. coli* DNA polymerase II include, but are not limited to, a group of DNA polymerases that are called Family B DNA polymerases (Braithwaite, D. K. and Ito, J. (1993) *Nucl. Acids Res.* 21, 787–802). Of particular relevance are the DNA polymerases from phages T2 and T6 which have extensive protein sequence homology to T4 DNA polymerase. Another extension of methods described here is that DNA polymerases with functional similarities to T4 DNA polymerase and *E. coli* DNA polymerase II may also be used to produce DNA sequence information with the chain-terminating nucleotides and methods disclosed hereinafter.

In accordance with another aspect of this invention there is provided a method to identify DNA polymerase modifications, having one or more specific amino acid substitutions in the polymerase protein sequence, that improve a given DNA polymerase in terms of DNA sequencing applications.

DETAILED DESCRIPTION OF THE INVENTION

Figure 1:
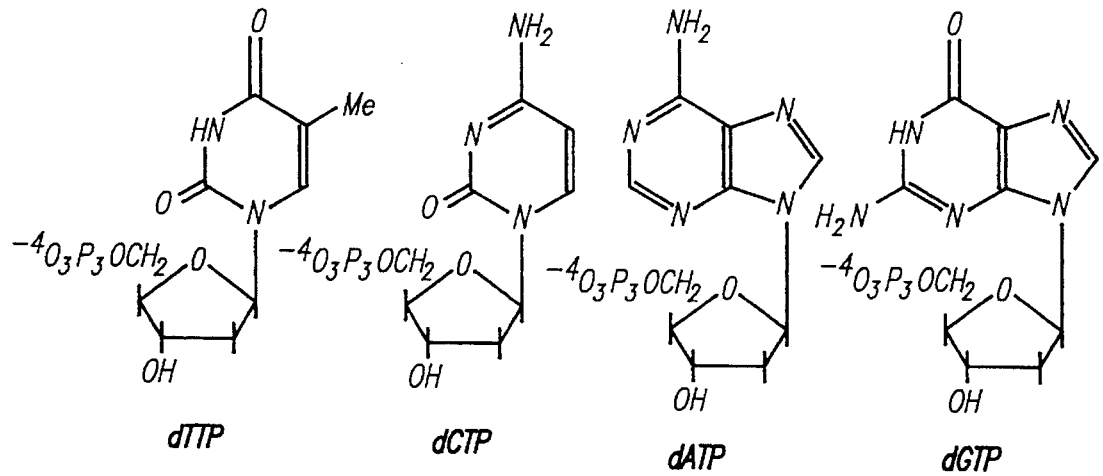
FIG. 1 depicts the structure of standard nucleotides and nucleotide analogs useful in the practice of the invention.
Figure 1:
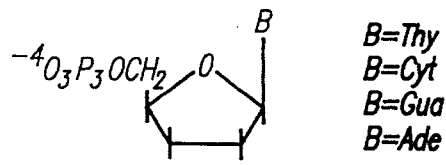
Figure 1:
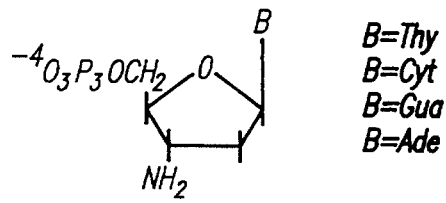
Figure 1:
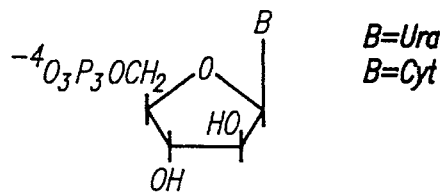
Figure 1:
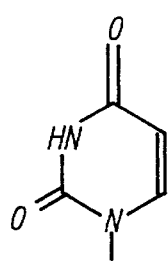

An aspect of the invention, namely to identify modified DNA polymerases with new properties that improve the ability of the modified DNA polymerases to carry out DNA sequencing reactions, is achieved by the design of a new genetic selection strategy that identifies modified DNA polymerases with superior DNA replication activities. The new genetic selection strategy has been designed around the T4 DNA polymerase.

T4 DNA polymerase (SEQ ID NO: 3 and 4) and *E. coli* DNA polymerase II (SEQ ID NO: 5 and 6), which have heretofore been unable to be used as sequencing polymerases, can be used as DNA sequencing polymerases in Sanger-type reactions if non-standard or novel combinations of chain-terminating nucleotides are used. Further to this discovery is the finding that inactivation of 3'→5' exonuclease activity in T4 DNA polymerase and *E. coli* DNA polymerase II improves the quality of the DNA sequence information obtained. In a further aspect, additional polymerase modifications have been discovered, which when combined with other modifications that reduce 3'→5' exonuclease activity, have the potential to produce a multiply modified DNA polymerase with advantageous DNA sequencing properties. Due to extensive sequence homology with T4 DNA polymerase, DNA polymerases such as phages T2 (SEQ ID NO: 1 and 2) and T6 DNA polymerases are particularly suitable in the application of the methods of the invention.

T4 DNA polymerase and *E. coli* DNA polymerase II can be used as effective DNA sequencing polymerases if the arabinonucleotides (FIG. 1), araUTP and araCTP, are used in place of the standard chain-terminating nucleotides ddTTP and ddCTP. The standard purine dideoxynucleotides (FIG. 1), ddATP and ddGTP, are effective chain-terminating nucleotides for T4 DNA polymerase and *E. coli* DNA polymerase II. DNA sequencing reactions for T4 DNA polymerase and *E. coli* DNA polymerase II differ from standard DNA sequencing reactions in that a novel combination of chain-terminating nucleotides is used. Although in principle any chain-terminating nucleotide may be used, DNA polymerases differ markedly in their ability to incorporate these nucleotides into the DNA chain. For T4 DNA polymerase and *E. coli* DNA polymerase II, the low incorporation of ddTTP and ddCTP by these enzymes have prevented the use of these standard chain-terminating nucleotides in sequencing protocols. The discovery that alternative chain-terminating arabinonucleotides, araCTP and araUTP, can be incorporated relatively efficiently by T4 DNA polymerase and *E. coli* DNA polymerase II enables these DNA polymerases to be used as sequencing polymerases. The DNA sequencing method that uses reactions with the novel combinations of chain-terminating nucleotides—araCTP, araUTP, ddATP and ddGTP, is described, hereinbelow, in Method I.

A further discovery is that inactivation or significant reduction of the 3'→5' exonuclease activity of T4 DNA polymerase and *E. coli* DNA polymerase II enhances the quality of DNA sequence information obtained using the Method I sequencing reactions. T4 DNA polymerase 3'→5' exonuclease activity can be significantly reduced by an amino acid substitution including, but not limited to, one or more of the following amino acid substitutions in the enzyme: D112A +E114A, D219A and D324A. In the above nomenclature which is used herein throughout, the single letter code for amino acids is used. The numbers flanked by the single letter codes for amino acids are the codon numbers. For example, D112A+E114A indicates an alanine (A) substitution for aspartate (D) at codon position 112. D112A+ E114A indicates two amino acid substitutions in the modified DNA polymerase. To achieve these variants the following mutations were employed: for D112A the A nucleotide at position 334 is replaced with a C nucleotide thereby effecting a change of the D amino acid to an A amino acid, as is known to one of ordinary skill in the art other nucleotide changes are capable of effecting the same change; for E114A the A nucleotide at position 340 is replaced with a C nucleotide, as is known other nucleotide changes can effect the same amino acid change; for D219A the A and C nucleotides at position 655 and 656, respectively, are replaced with a C and a G nucleotide, respectively, as is known other nucleotide changes can effect the same amino acid change; and for D324A the A nucleotide at position 970 is replaced with a C nucleotide, as is known other nucleotide changes can effect the same amino acid change. *E. coli* DNA polymerase II 3'→5' exonuclease activity can be significantly reduced by an amino acid substitution including, but not limited to, the following amino acid substitutions: D156A+E158A. To achieve these variants the following mutations were employed: for D156A the A nucleotide at position 467 is replaced with a C nucleotide, as is known other nucleotide changes can effect the same amino acid change; for E158A the A nucleotide at position 473 is replaced with a C nucleotide, as is known other nucleotide changes can effect the same amino acid change. Construction of 3'→5' exonuclease deficient variants of T4 DNA polymerase and *E. coli* DNA polymerase II is achieved by standard oligonucleotide mutagenesis procedures (for example, Kunkle, T. A., Roberts, J. D. and Zakour, R. A. (1987) *Method. Enz.* 154, 367–382).

Another aspect of the invention may be achieved by using chain-terminating nucleotides that are not used in standard DNA sequencing reactions. T4 DNA polymerase and *E. coli* DNA polymerase II may also be used as effective DNA sequencing polymerases if 3'amino- 2',3'-dideoxyribonucleotides (3'- NH$_2$dNTPs) (FIG. 1) are used in place of the standard ddNTPs. This sequencing method is described herein below in Method II. Unmodified (wild type) T4 DNA polymerase and 3'→5 ' exonuclease deficient variants can be used in Method II reactions; the 3'→5' exonuclease deficient variant of *E. coli* DNA polymerase II has also been successfully used in Method II reactions.

The 3'→5' exonuclease deficient form of T4 DNA polymerase can also be used to produce DNA sequence information without nucleotide analogs if the concentration of one of the four standard dNTPs is very low. For example, if the concentrations of dGTP, dCTP and dTTP are at 100 μM and the concentration of dATP is at 0.1 μM to 1 μM then sequencing products are observed that terminate one position before dATP is required for incorporation. With parallel reactions, each with one dNTP present at low concentration and the other three dNTPs present at high concentrations, the DNA sequence can be determined. This sequencing method is referred to hereinafter as Method III.

The third objective, namely to identify variant or modified DNA polymerases with new properties that enable the polymerases to have enhanced sequencing properties, has been achieved by designing a new strategy to select for novel DNA polymerases. The new strategy, a type of genetic selection, was developed for phage T4. The basic strategy begins with a phage T4 strain that has one or more mutations in the DNA polymerase gene which result in a variant (mutant) DNA polymerase which is partially defective in some aspect of DNA replication. Several types of DNA polymerase modifications can reduce the ability of DNA polymerase to replicate DNA efficiently. For example, alterations in the ability of the DNA polymerase to bind DNA template or dNTPs or in the ability of the DNA polymerase to translocate along the DNA template will reduce DNA replication efficiency. For phage T4, DNA polymerase mutants with reduced DNA replication activity can be readily identified. Phage T4 strains with mutant DNA polymerases that are partially defective in DNA replication cannot synthesize DNA if the bacterial host used in the infection contains the optA1 mutation. In other words, the $E.$ $coli$ optA1 host restricts growth of T4 strains with mutant DNA polymerases defective in DNA replication activity. The basis of the restriction observed for the $E.$ $coli$ optA1 strain is that increased amounts of an enzyme that degrades dGTP is produced (Wurgler, S. S., and Richardson, C. C. (1990) $Proc.$ $Natl.$ $Acad.$ $Sci.$ $U.S.A.$ 87, 2740–2744). Thus, phage T4 strains with variant DNA polymerases with reduced DNA replication activity cannot replicate DNA and produce phage progeny if the nucleotide pools, especially dGTP, are reduced.

In terms of development of a genetic selection strategy, conditions have been established which can be used to identify DNA replication defective DNA polymerases as well as to restrict production of progeny from phages with such defective DNA polymerases, namely the restricted production of phage progeny in infections of the $E.$ $coli$ optA1 bacterial host. These conditions, described hereinbelow, enable the selection of further modified (mutated) DNA polymerases with superior DNA replication ability. If the variant DNA polymerases with reduced DNA replication activity are further modified, for example by one or more additional amino acid substitutions, it may be that additional mutations/amino acid substitutions correct or compensate for the initial defect in DNA replication activity. Such further modified DNA polymerases will now be able to replicate DNA in the $E.$ $coli$ optA1 host and phage progeny will be produced. Thus, detection of phage progeny on the $E.$ $coli$ optA1 host in infections with phage formerly restricted from producing progeny on this host allows for the selection of multiply mutant DNA polymerases that have the starting mutation (amino acid substitutions that decrease DNA replication activity) plus one or more new mutations that encode additional amino acid substitutions that correct or compensate for the starting DNA replication defect. The new correcting or compensating mutations (also called suppressor mutations in genetic terminology) can be identified by sequencing the phage DNA polymerase gene using standard procedures (McPheeters, D. S., Christensen, A., Young, E. T., Stormo, G., and Gold, L. (1986) $Nucleic$ $Acid$ $Res.$ 14, 5813–5826; Reha-Krantz, L. J. (1988) $J.$ $Mol.$ $Biol.$ 202, 711–724). The new mutations can be introduced into the phage T4 DNA polymerase gene or into T4 DNA polymerase expression vectors for further study. In contrast to the starting phage T4 DNA polymerases with reduced DNA replication ability, the new variant DNA polymerases have superior DNA replication ability because these variant DNA polymerases were selected on the basis of their ability to overcome, compensate or correct defects in variant DNA polymerase with reduced DNA replication activity. The genetic strategy to identify variant DNA polymerases with superior DNA replication abilities is highly sensitive as a single phage with the above described properties can be selected from a population of $10^8$ to $10^9$ phage.

Further to the invention, variant DNA polymerases with superior DNA replication activity have properties advantageous for DNA sequencing polymerase, such as enhanced primer extension which produces a more uniform distribution of sequencing products and enhanced DNA replication in template regions that may block or hinder replication by unmodified DNA polymerases. T4 DNA polymerase variants with superior DNA replication ability are predicted to improve the quality of DNA sequence information produced by Methods I, II, and III.

The genetic selection strategy described here for the detection of variant DNA polymerases with superior DNA replication ability can be applied to the DNA polymerases of other organisms if such defective DNA polymerases can be identified and if variants with correcting or compensating mutations can be selected.

DNA Sequencing Method I.

T4 DNA polymerase with significantly reduced 3'→5' exonuclease activity, such as variant forms with either D112A+E114A, D219A, or D324A amino acid substitutions, and $E.$ $coli$ DNA polymerase II with significantly reduced 3'→5' exonuclease activity, such as the variant form with D156A+E158A amino acid substitutions, can be used as DNA sequencing polymerases with the following set of chain-terminating nucleotides: ddATP, ddGTP, araCTP, and araUTP (FIG. 1).

Figure 2A:
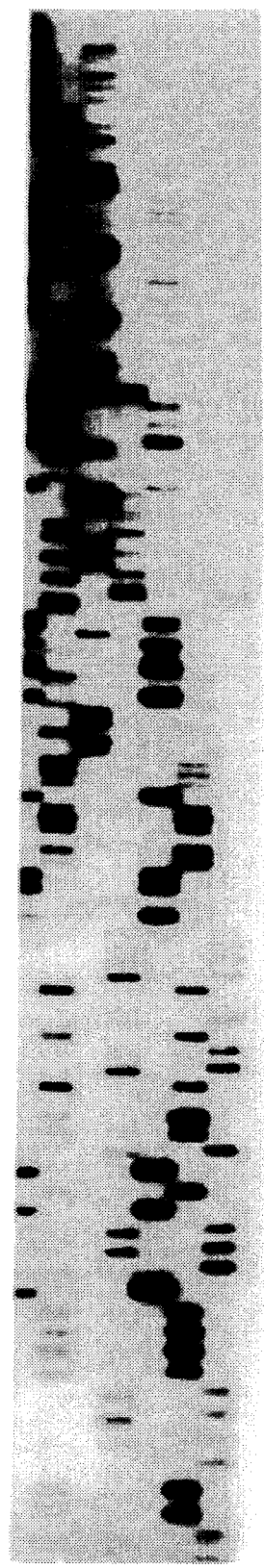
FIGS. 2A–2C depicts DNA sequencing gels which resulted from the use of variant *E. coli* DNA polymerase II and T4 DNA polymerase.
Figure 2B:
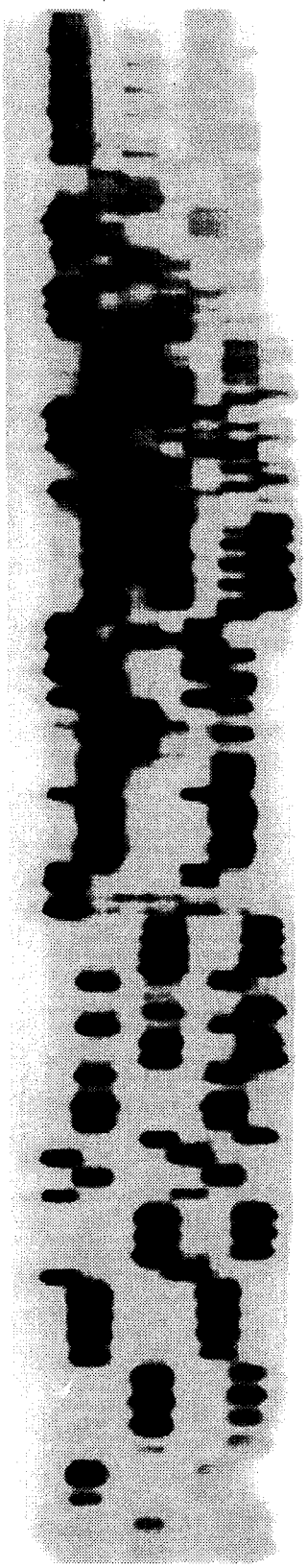
Figure 2C:

FIG. 2 shows photographs of three DNA sequencing gels. DNA sequencing patterns obtained with Method I are in panels A and B, lanes 1–4, and panel C. Panel A shows DNA sequencing reactions with the exonuclease deficient variant of $E.$ $coli$ DNA polymerase II. The reaction with ddGTP is in lane 1, the reaction with ddATP is in lane 2, the reaction with araCTP is in lane 3, and the reaction with araUTP is in lane 4. Panel B shows DNA sequencing reactions with the exonuclease deficient form of bacteriophage T4 DNA polymerase. Again, lane 1 has reactions with ddGTP, lane 2 has ddATP, lane 3 has araCTP, and lane 4 has araUTP. The reactions in panels A and B have $Mg^{2+}$ as the divalent metal cation. Sequencing patters are also obtained with $Mn^{2+}$ in place of $Mg^{2+}$. Method I reactions with $Mn^{2+}$ with the exonuclease deficient form of $E.$ $coli$ DNA polymerase II are shown on the left side of panel C, lanes 1–4; reactions with the exonuclease deficient form of T4 DNA polymerase are shown on the right side of panel C, lanes 1–4. Panel C, lanes 1–4 contain reactions with ddGTP (lane 1), ddATP (lane 2), araCTP (lane 3), and araUTP (lane 4).

DNA Sequencing Method II.

Wild type (unmodified) and 3'→5' exonuclease deficient forms of T4 DNA polymerase and the 3'→5 ' exonuclease deficient form of $E.$ $coli$ DNA polymerase II can be used as DNA sequencing polymerases with 3'amino- 2',3'-dideoxyribonucleotides (FIG. 1) as chain terminating nucleotides. Method II reactions for the exonuclease deficient form of $E.$ $coli$ DNA polymerase II are shown in FIG. 2, panel A, lanes 5–7. Lane five shows the reaction with 3'amino-2',3'-dideoxyGTP; lane 6 shows the reaction with 3'amino-2',3'-dideoxyATP; lane 7 shows the reaction with 3'amino-2',3-dideoxyTTP. Method II reactions for the exonuclease deficient form of T4 DNA polymerase are shown in panel B, lanes 5–7. Lane 5, 6 and 7 show reactions with 3'amino-2'3'dideoxyGTP, -ATP and -TTP, respectively.

The data demonstrate that the exonuclease deficient forms of E. coli DNA polymerase II and bacteriophage T4 DNA polymerases can produce DNA sequence information using a combination of the following chain-terminating nucleotides: ddGTP or 3'amino-2',3'-dideoxyGTP; ddATP or 3'amino-2',3'-dideoxyATP; araUTP or 3'amino-2',3'dideoxy-TTP; and araCTP. In view of the good sequence patterns obtained with 3'amino-2'3'dideoxy-GTP, -ATP and -TTP, it is likely that 3'amino-2+,3'-dideoxy-CTP will also be an effective chain-terminating nucleotide. No attempt was made to optimize conditions for Methods I or II in order to achieve equal band intensities or to increase the length of readable sequence for the reactions shown in FIG. 2. Nevertheless, the sequencing methods can provide sequence information for at least 300 bases. The exonuclease deficient form of T4 DNA polymerase is not required for sequencing reactions with the 3'amino- 2',3'-dideoxyribonucleoside triphosphates.

Sample Experimental conditions for Methods I and II (FIG. 2).

Labeling reaction.

5 µl exonuclease deficient DNA polymerase; 300–400 units/ml for T4 DNA polymerase or for E. coli DNA polymerase II. One unit T4 DNA polymerase catalyzes 10 nmol of dTMP incorporation into DNA in 30 min at 30° C. One unit of E. coli DNA polymerase II catalyzes the incorporation of 1 pmol of dTMP into DNA in 1 min at 37° C. Although the reaction is typically conducted at 37° C., the reaction may be conducted in a temperature range from about 35° C. to about 42° C.

15 µl primer-M13 DNA complex, 15 nM

15 µl labeling reaction solution: 2 µM dGTP, dCTP, dTTP; 1 µM [$\alpha^{32}$P]dATP; 50 mM Tris-HCl (pH 8.5); 5 mM $MgCl_2$ or 6 mM $MnCl_2$ for E. coli DNA polymerase II; 5 mM $MgCl_2$ or 0.5 mM $MnCl_2$ for T4 DNA polymerase; 5 mM dithiothreitol; 50 µg/ml bovine serum albumin.

The reaction mixtures were incubated 5 min at 37° C.

The primer may also be labeled at the 5'-end, or by including a labeled nucleotide in the extension reaction and by other standard methods.

Extension Reaction.

4 µl labeling reaction mixture (from above)

4 µl termination solution: 50 µM dGTP, dATP, dCTP and dTTP; and one of the termination analogs listed below:

Method I: ddGTP, 1.6 mM; ddATP, 0.7 mM; araCTP, 0.5 mM; araUTP, 0.5mM.

Method II: 3'-amino-2',3'-dideoxyGTP, 0.5 mM; 3'-amino-2',3'-dideoxyATP, 0 5 mM; 3'-amino-2',3'-dideoxyTTP, 0.5 mM Reactions were incubated at 5 min at 37° C. Reactions were stopped by adding formamide/EDTA.

Figure 3:
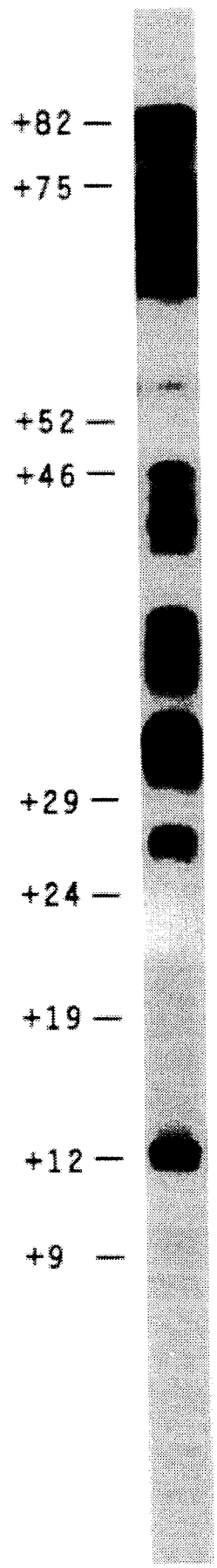
FIG. 3 depicts a DNA sequencing gel in which dATP is used at very low concentrations compared to the other standard nucleotides.

DNA sequencing Method III (FIG. 3).

Exonuclease deficient T4 DNA polymerase can produce DNA sequence information in reactions where one dNTP is at a low concentration (for example, 0.1 µM to 1 µM) and the other three dNTPs are at high concentrations (100 µM) (FIG. 3). DNA sequencing patterns are produced as with sequencing reactions with nucleotide analogs except that sequencing products produced by this method terminate one position before the dNTP at low concentrations is required.

Sample Experimental conditions:
 25 mM Hepes (pH 7.5)
 60 mM NaOAc
 1 mM dithiothreitol
 100 µM dGTP, dCTP and dTTP
 0.1 µM dATP (1 µM dATP for longer DNA products)
 0.2 mg/ml bovine serum albumin
 7.5 nM 5'[$^{32}$P]labeled primer-template (expressed as the concentration of 3'-primer termini)
 30 nM exonuclease deficient T4 DNA polymerase
 6 mM $Mg(OAc)_2$ The reaction shown in FIG. 3 contained 0.1 µM dATP and was incubated for 1 min at 30° C. Conditions have not been optimized to obtain high amounts of sequence information; however, reactions in which the low concentration dNTP is at 1 µM yield sequence information greater than 100 bases.

Isolation of Novel T4 DNA Polymerases with Properties Advantageous for DNA Sequencing.

The first step in this aspect of the invention is to identify T4 strains with variant (mutant) DNA polymerases defective in some aspect of DNA replication. T4 strains with mutant DNA polymerase that have the amino acid substitutions listed below were chosen, but the genetic selection strategy is not limited to these mutants as any mutant DNA polymerase with defective DNA replication ability can be used. Variant (mutant) T4 DNA polymerases that are partially defective in some aspect of DNA replication cannot replicate DNA in the E. coli optA1 host.

T4 strains with mutant DNA polymerases with amino acid substitutions W213S, I417V, A737V or A777V cannot replicate DNA in the E. coli optA1 host. To achieve these variants the following mutations were employed: for W213S the G nucleotide at position 637 is replaced with a C nucleotide; for I417V the A nucleotide at position 1249 is replaced with a G nucleotide; for A737V the C nucleotide at position 2209 is replaced with a T nucleotide; and for A777V the C nucleotide at position 2329 is replaced with a T nucleotide. As is known other nucleotide replacements can cause the same amino acid changes.

The second step is to select T4 strains that can replicate DNA in the E. coli optA1 host even though the DNA polymerase still retains the amino acid substitution that alone reduces DNA replication ability and prevents replication of DNA in E. coli optA1 host. T4 strains that have acquired a second DNA polymerase mutation (or multiple mutations), either by spontaneous mutation or by mutagenesis treatment, that encodes a new amino acid substitution that can correct or compensate the DNA replication defect produced by the first amino acid substitution, will be able to replicate DNA in the E. coli optA1 host and produce phage progeny. DNA polymerases thus identified have at least two amino acid substitutions: the starting amino acid substitution and one or more new amino acid substitutions that restore DNA replication activity. This genetic selection strategy is of high sensitivity. A phage with a mutant DNA polymerase containing the starting amino acid substitution and the amino acid substitution(s) that restores DNA replication activity can be selected from a population of $10^8$ to $10^9$ phage.

The third step is to identify the DNA replication restoring mutation(s). This step utilizes standard sequencing procedures to find the new mutation(s) in the T4 DNA polymerase gene. Once the new mutation(s) has been identified, the mutation can be introduced into phage or into T4 DNA polymerase expression vectors using standard procedures. Unlike the starting, DNA replication defective DNA polymerase, the DNA polymerases with the correcting or compensating amino acid substitutions have superior DNA replication activity. A sample of the amino acid substitutions discovered using the genetic selection strategy described above include but are not limited to: I50L, G82D, G255S and E743K. To achieve these variants the following mutations were employed: for I50L the A nucleotide at position 148 is replaced with a C nucleotide; for G82D the G nucleotide at position 244 is replaced with an A nucleotide; for G255S the G nucleotide at position 763 is replaced with an A nucleotide; and for E743K the G nucleotide at position 2227 is replaced with an A nucleotide. As is known other nucleotide replacements can effect the same amino acid changes.

Variant (mutant, modified) T4 DNA polymerases with amino acid substitutions that confer enhanced DNA replication activity have new properties advantageous for DNA sequencing. One frequent DNA sequencing problem is that DNA polymerases used in sequencing reactions pause or disassociate at some template sites. As a consequence of this premature stop in chain elongation, sequencing products are produced that are not terminated by a chain-terminating nucleotide. Another problem is that DNA polymerase incorporation of nucleotides and chain-terminating nucleotides is affected by the template sequence which may lead to an unequal distribution of sequencing products. Novel DNA polymerases with enhanced DNA replication activity may surmount these problems. The G82D-T4 DNA polymerase (also known as T4 mel 62 DNA polymerase) has been tested in primer extension assays and this novel DNA polymerase has been found to extend primers that are problematic for the wild type T4 DNA polymerase. An example of G82D-T4 DNA polymerase synthesis is given in FIG. 4.

Figure 4:
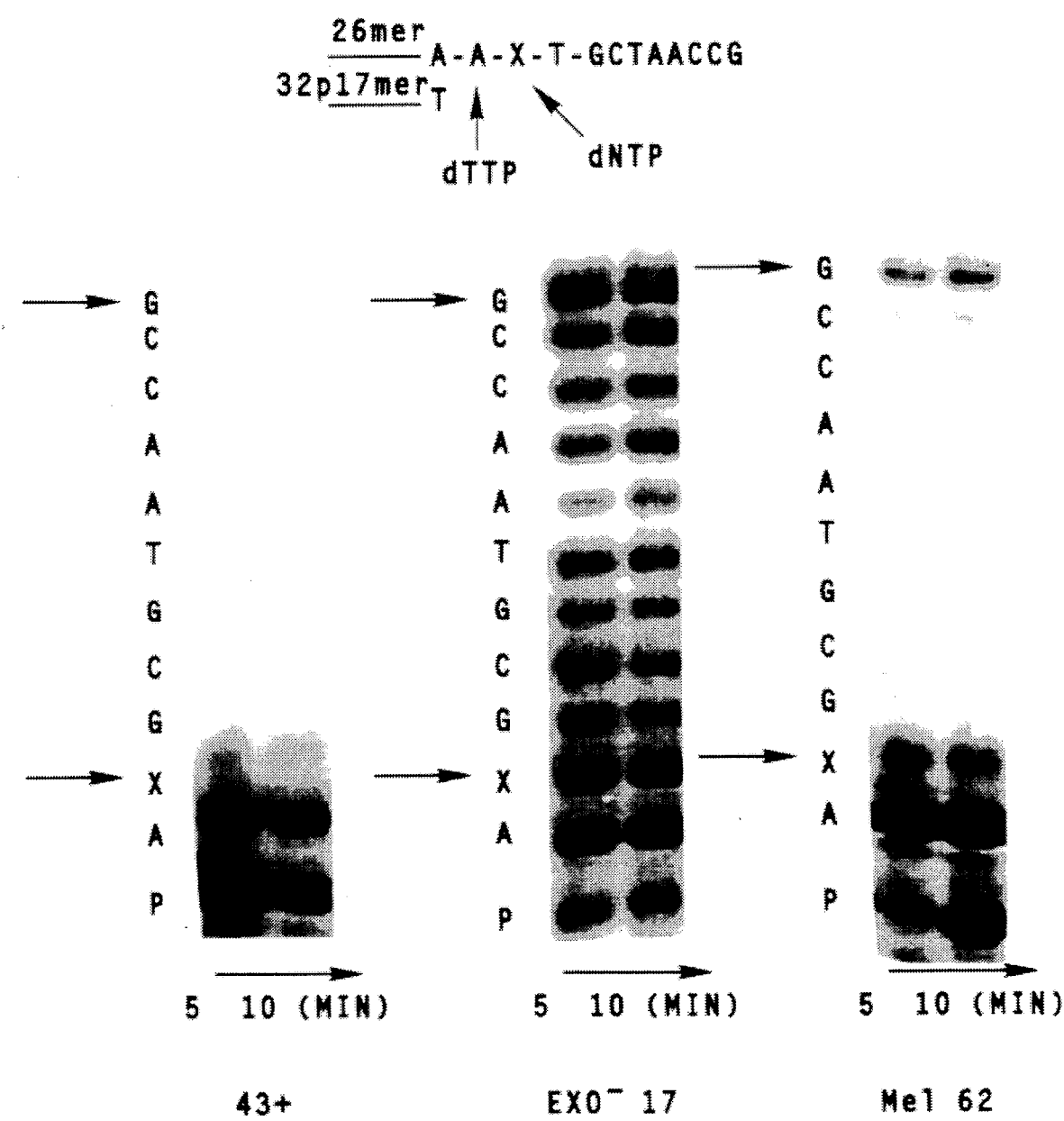
FIG. 4 depicts primer extension past a template abasic site (X) by wild-type and mutant T4 DNA polymerases.

FIG. 4 depicts the use of three T4 polymerases to copy a DNA template lesion (an abasic lesion—a base is missing on the template strand, indicated by X). The wild-type T4 polymerase has difficulty incorporating a nucleotide opposite X, as shown by the very light bands. A 3'-exonuclease deficient T4 polymerase mutant, EXO⁻17, is able to incorporate nucleotides opposite X (note the intense band at X) and continue synthesis beyond the lesion. The T4 mel 62 polymerase is a mutant enzyme (it conveys a mutator phenotype in vivo) that has apparent normal (wild-type) levels of 3'-exonuclease and polymerase activities. It nevertheless is also able to incorporate nucleotides opposite X and to continue synthesis beyond X. What is most interesting is that the absence of "pausing" bands beyond X suggests that the mel 62 DNA polymerase remains bound to the primer template DNA more tightly than either EXO⁻17 or the wild-type polymerases. Thus, it is possible that this enzyme may be able to overcome template and substrate obstacles to synthesize long stretches of DNA.

It is contemplated that one or more amino acid substitutions that confer superior DNA replication activity will be combined with one or more amino acid substitutions that significantly reduce 3'→5' exonuclease activity to create a multiply modified novel T4 DNA polymerase with several properties that are advantageous for DNA sequencing polymerases.

It is known that polymerases, such as bacteriophage T7 DNA polymerase, may be used in conjunction with their accessory proteins thereby increasing the processivity of the polymerase by decreasing the rate of disassociation of the polymerase from the DNA strand to be sequenced.

In the case of the T4 polymerase, its accessory proteins, include but are not limited to, the following T4 gene products: gene product 32, 41, 45 and the 44/62 complex. In the case of E. coli DNA polymerase II, the accessory proteins are the following: β protein; the γ protein complex wherein the γ complex is composed of γ, δ, δ', χ,Ψ; and SSB (single stranded binding protein) (note that β protein and γ complex are E. coli pol III accessory proteins). Use of these accessory proteins enhances the efficiency of the polymerases in sequencing DNA.

While there have been shown and described the fundamental novel features of the invention, it will be understood that various omissions, substitutions and changes in the form and details illustrated may be made by those skilled in the art without departing from the spirit of the invention. It is the intention, therefore, to be limited only as indicated by the scope of the following claims.

We claim:

1. A method for sequencing DNA, comprising:

contacting a polymerase selected from the group consisting of T4 polymerase, T2 polymerase, T6 polymerase and *E. coli* DNA polymerase II, with a primed DNA strand to be sequenced in the presence of dATP, dGTP, dCTP, dTTP, a first chain-terminating nucleotide, a second chain-terminating nucleotide, a third chain-terminating nucleotide and a fourth chain-terminating nucleotide; and allowing said contacting to proceed under reaction conditions to maintain polymerase activity for a period of time sufficient to obtain sequencing information, wherein said first chain-terminating nucleotide is 3'-amino-2',3'dideoxy-ATP, said second chain-terminating nucleotide is 3'-amino- 2',3'dideoxy-GTP, said third chain-terminating nucleotide is 3'-amino-2',3'dideoxy-CTP and said fourth chain-terminating nucleotide is 3'-amino- 2',3'dideoxy-TTP.

2. The method of claim 1, wherein the polymerase is a variant T4 polymerase selected from the group consisting of I50L, G 82D, D112A+E114A, D156A +E158A, D219A, G255S, D324A and E743K.

3. The method of claim 1, wherein the polymerase is selected from the group consisting of T4 polymerase, T2 polymerase and T6 polymerase.

4. The method according to claim 3, wherein the polymerase is used in conjunction with at least one accessory protein selected from the group consisting of T4 gene products 32, 41, 45 and the 44/62 complex.

5. The method of claim 1, wherein the polymerase is selected from the group consisting of *E. coli* DNA polymerase II.

6. The method of claim 5, wherein the polymerase is used in conjunction with at least one accessory protein selected from the group consisting of β protein, gamma complex and SSB protein.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 2760 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..2760

( x i ) SEQUENCE DESCRIPTION: SEQ ID NO:1:

| CGT | CAT | CTT | CAT | TTT | TTT | TTT | TTT | TTT | TTT | TTT | TTT | TTT | TTT | TTT | TTT | 4 8 |
|---|---|---|---|---|---|---|---|---|---|---|---|---|---|---|---|---|
| Arg | His | Leu | His | Phe | Phe | Phe | Phe | Phe | Phe | Phe | Phe | Phe | Phe | Phe | Phe | |
| 1 | | | | 5 | | | | | 1 0 | | | | | | 1 5 | |

| | | | | | | | | | | | | | | | | |
|---|---|---|---|---|---|---|---|---|---|---|---|---|---|---|---|---|
| TTT | TTT | TTT | TTT | ATT | ATT | ATG | AAA | GAA | TTT | TAT | ATC | TCT | ATC | GAA | ACA | 96 |
| Phe | Phe | Phe | Phe | Ile | Ile | Met | Lys | Glu | Phe | Tyr | Ile | Ser | Ile | Glu | Thr | |
| | | | 20 | | | | | 25 | | | | | 30 | | | |
| GTC | GGA | AAT | AAT | ATT | ATT | GAA | CGT | TAT | ATT | GAT | GAA | AAC | GGA | AAG | GAA | 144 |
| Val | Gly | Asn | Asn | Ile | Ile | Glu | Arg | Tyr | Ile | Asp | Glu | Asn | Gly | Lys | Glu | |
| | | 35 | | | | | 40 | | | | | 45 | | | | |
| CGT | ACT | CGT | GAA | GTA | GAA | TAT | CTT | CCG | ACT | ATG | TTT | AGG | CAT | TGT | AAG | 192 |
| Arg | Thr | Arg | Glu | Val | Glu | Tyr | Leu | Pro | Thr | Met | Phe | Arg | His | Cys | Lys | |
| | | 50 | | | | | 55 | | | | | 60 | | | | |
| GAA | GAG | TCA | AAA | TAC | AAA | GAC | ATC | TAT | GGT | AAA | AAC | TGT | GCT | CCT | CAA | 240 |
| Glu | Glu | Ser | Lys | Tyr | Lys | Asp | Ile | Tyr | Gly | Lys | Asn | Cys | Ala | Pro | Gln | |
| 65 | | | | 70 | | | | | 75 | | | | | | 80 | |
| AAA | TTT | CCA | TCA | ATG | AAA | GAT | GCT | CGA | GAT | TGG | ATG | AAG | CGA | ATG | GAA | 288 |
| Lys | Phe | Pro | Ser | Met | Lys | Asp | Ala | Arg | Asp | Trp | Met | Lys | Arg | Met | Glu | |
| | | | | 85 | | | | | 90 | | | | | 95 | | |
| GAC | ATC | GGT | CTC | GAA | GCT | CTC | GGT | ATG | AAC | GAT | TTT | AAA | CTC | GCT | TAT | 336 |
| Asp | Ile | Gly | Leu | Glu | Ala | Leu | Gly | Met | Asn | Asp | Phe | Lys | Leu | Ala | Tyr | |
| | | | 100 | | | | | 105 | | | | | 110 | | | |
| ATC | AGT | GAT | ACG | TAT | GGT | TCA | GAA | ATT | GTT | TAT | GAC | CGA | AAA | TTT | GTT | 384 |
| Ile | Ser | Asp | Thr | Tyr | Gly | Ser | Glu | Ile | Val | Tyr | Asp | Arg | Lys | Phe | Val | |
| | | 115 | | | | | 120 | | | | | 125 | | | | |
| CGT | GTA | GCT | AAC | TGT | GAC | ATT | GAG | GTT | ACT | GGT | GAT | AAA | TTT | CCT | GAC | 432 |
| Arg | Val | Ala | Asn | Cys | Asp | Ile | Glu | Val | Thr | Gly | Asp | Lys | Phe | Pro | Asp | |
| | 130 | | | | | 135 | | | | | 140 | | | | | |
| CCA | ATG | AAA | GCA | GAA | TAT | GAA | ATT | GAT | GCT | ATC | ACT | CAT | TAT | GAT | TCA | 480 |
| Pro | Met | Lys | Ala | Glu | Tyr | Glu | Ile | Asp | Ala | Ile | Thr | His | Tyr | Asp | Ser | |
| 145 | | | | 150 | | | | | 155 | | | | | | 160 | |
| ATT | GAC | GAC | CGT | TTT | TAT | GTT | TTC | GAC | CTT | TTG | AAT | TCA | ATG | TAC | GGT | 528 |
| Ile | Asp | Asp | Arg | Phe | Tyr | Val | Phe | Asp | Leu | Leu | Asn | Ser | Met | Tyr | Gly | |
| | | | | 165 | | | | | 170 | | | | | 175 | | |
| TCA | GTA | TCA | AAA | TGG | GAT | GCA | AAG | TTA | GCT | GCT | AAG | CTT | GAC | TGT | GAA | 576 |
| Ser | Val | Ser | Lys | Trp | Asp | Ala | Lys | Leu | Ala | Ala | Lys | Leu | Asp | Cys | Glu | |
| | | | 180 | | | | | 185 | | | | | 190 | | | |
| GGT | GGT | GAT | GAA | GTT | CCT | CAA | GAA | ATT | CTT | GAC | CGA | GTA | ATT | TAT | ATG | 624 |
| Gly | Gly | Asp | Glu | Val | Pro | Gln | Glu | Ile | Leu | Asp | Arg | Val | Ile | Tyr | Met | |
| | | 195 | | | | | 200 | | | | | 205 | | | | |
| CCA | TTT | GAT | AAT | GAG | CGT | GAT | ATG | CTC | ATG | GAA | TAT | ATT | AAT | CTC | TGG | 672 |
| Pro | Phe | Asp | Asn | Glu | Arg | Asp | Met | Leu | Met | Glu | Tyr | Ile | Asn | Leu | Trp | |
| | 210 | | | | | 215 | | | | | 220 | | | | | |
| GAA | CAG | AAA | CGA | CCT | GCT | ATT | TTT | ACT | GGT | TGG | AAT | ATT | GAG | GGG | TTT | 720 |
| Glu | Gln | Lys | Arg | Pro | Ala | Ile | Phe | Thr | Gly | Trp | Asn | Ile | Glu | Gly | Phe | |
| 225 | | | | | 230 | | | | | 235 | | | | | 240 | |
| GAC | GTT | CCG | TAT | ATC | ATG | AAT | CGC | GTT | AAA | ATG | ATT | CTG | GGT | GAA | CGC | 768 |
| Asp | Val | Pro | Tyr | Ile | Met | Asn | Arg | Val | Lys | Met | Ile | Leu | Gly | Glu | Arg | |
| | | | | 245 | | | | | 250 | | | | | 255 | | |
| AGT | ATG | AAA | CGT | TTC | TCT | CCA | ATC | GGT | CGG | GTA | AAA | TCT | AAA | CTA | ATT | 816 |
| Ser | Met | Lys | Arg | Phe | Ser | Pro | Ile | Gly | Arg | Val | Lys | Ser | Lys | Leu | Ile | |
| | | | 260 | | | | | 265 | | | | | 270 | | | |
| CAA | AAT | ATG | TAC | GGT | AGC | AAA | GAA | ATT | TAT | TCT | ATT | GAT | GGC | GTA | TCT | 864 |
| Gln | Asn | Met | Tyr | Gly | Ser | Lys | Glu | Ile | Tyr | Ser | Ile | Asp | Gly | Val | Ser | |
| | | 275 | | | | | 280 | | | | | 285 | | | | |
| ATT | CTT | GAT | TAT | TTA | GAT | TTG | TAC | AAG | AAA | TTC | GCT | TTT | ACT | AAT | TTG | 912 |
| Ile | Leu | Asp | Tyr | Leu | Asp | Leu | Tyr | Lys | Lys | Phe | Ala | Phe | Thr | Asn | Leu | |
| | 290 | | | | | 295 | | | | | 300 | | | | | |
| CCG | TCA | TTC | TCT | TTG | GAA | TCA | GTT | GCT | CAA | CAT | GAA | ACC | AAA | AAA | GGT | 960 |
| Pro | Ser | Phe | Ser | Leu | Glu | Ser | Val | Ala | Gln | His | Glu | Thr | Lys | Lys | Gly | |
| 305 | | | | | 310 | | | | | 315 | | | | | 320 | |
| AAA | TTA | CCA | TAC | GAC | GGT | CCT | ATT | AAT | AAA | CTT | CGT | GAG | ACT | AAT | CAT | 1008 |
| Lys | Leu | Pro | Tyr | Asp | Gly | Pro | Ile | Asn | Lys | Leu | Arg | Glu | Thr | Asn | His | |
| | | | | 325 | | | | | 330 | | | | | 335 | | |

```
CAA CGA TAC ATT AGT TAT AAC ATC ATT GAC GTA GAA TCA GTT CAA GCA    1056
Gln Arg Tyr Ile Ser Tyr Asn Ile Ile Asp Val Glu Ser Val Gln Ala
            340             345             350

ATT GAT AAA ATT CGT GGG TTT ATC GAT CTA GTT TTA AGT ATG TCT TAT    1104
Ile Asp Lys Ile Arg Gly Phe Ile Asp Leu Val Leu Ser Met Ser Tyr
            355             360             365

TAT GCT AAA ATG CCT TTT TCT GGT GTA ATG AGT CCT ATT AAA ACT TGG    1152
Tyr Ala Lys Met Pro Phe Ser Gly Val Met Ser Pro Ile Lys Thr Trp
    370             375             380

GAT GCT ATT ATT TTT AAC TCA TTG AAA GGT GAA CAC AAG GTT ATT CCT    1200
Asp Ala Ile Ile Phe Asn Ser Leu Lys Gly Glu His Lys Val Ile Pro
385             390             395             400

CAA CAA GGT TCG CAC GTT AAA CAG AGT TTT CCG GGT GCA TTT GTA TTT    1248
Gln Gln Gly Ser His Val Lys Gln Ser Phe Pro Gly Ala Phe Val Phe
                405             410             415

GAA CCT AAA CCA ATT GCT CGT CGA TAC ATT ATG AGT TTT GAC TTG ACG    1296
Glu Pro Lys Pro Ile Ala Arg Arg Tyr Ile Met Ser Phe Asp Leu Thr
            420             425             430

TCT CTG TAT CCG AGC ATT ATT CGC CAG GTT AAC ATT AGT CCT GAA ACT    1344
Ser Leu Tyr Pro Ser Ile Ile Arg Gln Val Asn Ile Ser Pro Glu Thr
            435             440             445

ATT CGT GGT CAG TTT AAA GTT CAT CCA ATT CAT GAA TAT ATC GCA GGA    1392
Ile Arg Gly Gln Phe Lys Val His Pro Ile His Glu Tyr Ile Ala Gly
450             455             460

ACA GCT CCT AAA CCA AGT GAT GAA TAT TCT TGT TCT CCG AAT GGA TGG    1440
Thr Ala Pro Lys Pro Ser Asp Glu Tyr Ser Cys Ser Pro Asn Gly Trp
465             470             475             480

ATG TAT GAT AAG CAT CAA GAA GGT ATC ATT CCA AAG GAA ATC GCT AAA    1488
Met Tyr Asp Lys His Gln Glu Gly Ile Ile Pro Lys Glu Ile Ala Lys
                485             490             495

GTA TTT TTC CAG CGT AAA GAT TGG AAA AAG AAA ATG TTC GCT GAA GAA    1536
Val Phe Phe Gln Arg Lys Asp Trp Lys Lys Lys Met Phe Ala Glu Glu
            500             505             510

ATG AAT GCC GAA GCT ATT AAA AAG ATT ATT ATG AAA GGC GCA GGG TCT    1584
Met Asn Ala Glu Ala Ile Lys Lys Ile Ile Met Lys Gly Ala Gly Ser
            515             520             525

TGT TCA ACT AAA CCA GAA GTT GAA CGA TAT GTT AAG TTC ACT GAT GAT    1632
Cys Ser Thr Lys Pro Glu Val Glu Arg Tyr Val Lys Phe Thr Asp Asp
530             535             540

TTC TTA AAT GAA CTA TCG AAT TAT ACT GAA TCT GTT CTT AAT AGT CTG    1680
Phe Leu Asn Glu Leu Ser Asn Tyr Thr Glu Ser Val Leu Asn Ser Leu
545             550             555             560

ATT GAA GAA TGT GAA AAA GCA GCT ACA CTT GCT AAT ACA AAT CAG CTG    1728
Ile Glu Glu Cys Glu Lys Ala Ala Thr Leu Ala Asn Thr Asn Gln Leu
                565             570             575

AAC CGT AAA ATT CTT ATT AAC AGT CTT TAT GGT GCT CTT GGT AAT ATT    1776
Asn Arg Lys Ile Leu Ile Asn Ser Leu Tyr Gly Ala Leu Gly Asn Ile
            580             585             590

CAT TTC CGT TAC TAT GAT TTA CGA AAT GCT ACT GCT ATC ACA ATT TTT    1824
His Phe Arg Tyr Tyr Asp Leu Arg Asn Ala Thr Ala Ile Thr Ile Phe
            595             600             605

GGT CAA GTT GGT ATT CAG TGG ATT GCT CGT AAA ATT AAT GAA TAT CTG    1872
Gly Gln Val Gly Ile Gln Trp Ile Ala Arg Lys Ile Asn Glu Tyr Leu
610             615             620

AAT AAA GTA TGC GGA ACT AAT GAT GAA GAT TTC ATC GCA GCA GGT GAT    1920
Asn Lys Val Cys Gly Thr Asn Asp Glu Asp Phe Ile Ala Ala Gly Asp
625             630             635             640

ACT GAT TCG GTA TAT GTT TGT GTA GAT AAA GTT ATT GAA AAA GTT GGT    1968
Thr Asp Ser Val Tyr Val Cys Val Asp Lys Val Ile Glu Lys Val Gly
                645             650             655
```

| | | | | | | | | | | | | | | | | |
|---|---|---|---|---|---|---|---|---|---|---|---|---|---|---|---|---|
| CTT | GAC | CGA | TTC | AAA | GAG | CAG | AAC | GAT | TTG | GTT | GAA | TTC | ATG | AAT | CAG | 2016 |
| Leu | Asp | Arg | Phe 660 | Lys | Glu | Gln | Asn | Asp 665 | Leu | Val | Glu | Phe | Met 670 | Asn | Gln | |
| TTT | GGT | AAG | AAA | AAG | ATG | GAA | CCT | ATG | ATT | GAT | GTT | GCA | TAT | CGT | GAG | 2064 |
| Phe | Gly | Lys 675 | Lys | Lys | Met | Glu | Pro 680 | Met | Ile | Asp | Val | Ala 685 | Tyr | Arg | Glu | |
| TTA | TGT | GAT | TAT | ATG | AAT | AAC | CGC | GAG | CAT | CTG | ATG | CAT | ATG | GAC | CGT | 2112 |
| Leu | Cys 690 | Asp | Tyr | Met | Asn | Asn 695 | Arg | Glu | His | Leu | Met 700 | His | Met | Asp | Arg | |
| GAA | GCT | ATT | TCT | TGC | CCT | CCG | CTT | GGT | TCA | AAG | GGT | GTT | GGT | GGA | TTT | 2160 |
| Glu 705 | Ala | Ile | Ser | Cys | Pro 710 | Pro | Leu | Gly | Ser | Lys 715 | Gly | Val | Gly | Gly | Phe 720 | |
| TGG | AAA | GCG | AAA | AAA | CGT | TAT | GCT | CTG | AAC | GTT | TAT | GAT | ATG | GAA | GAT | 2208 |
| Trp | Lys | Ala | Lys | Lys 725 | Arg | Tyr | Ala | Leu | Asn 730 | Val | Tyr | Asp | Met | Glu 735 | Asp | |
| AAG | CGA | TTT | GCT | GAA | CCG | CAT | CTA | AAA | ATC | ATG | GGT | ATG | GAA | ACT | CAG | 2256 |
| Lys | Arg | Phe | Ala 740 | Glu | Pro | His | Leu | Lys 745 | Ile | Met | Gly | Met | Glu 750 | Thr | Gln | |
| CAG | AGT | TCA | ACA | CCA | AAA | GCA | GTG | CAA | GAA | GCA | CTC | GAA | GAA | AGT | ATT | 2304 |
| Gln | Ser | Ser 755 | Thr | Pro | Lys | Ala | Val 760 | Gln | Glu | Ala | Leu | Glu 765 | Glu | Ser | Ile | |
| CGT | CGT | ATT | CTT | CAG | GAA | GGC | GAA | GAG | TCT | GTC | CAA | GAA | TAT | TAC | AAG | 2352 |
| Arg | Arg 770 | Ile | Leu | Gln | Glu | Gly 775 | Glu | Glu | Ser | Val | Gln 780 | Glu | Tyr | Tyr | Lys | |
| AAC | TTC | GAG | AAA | GAA | TAT | CGT | CAA | CTT | GAC | TAT | AAA | GTT | ATT | GCT | GAA | 2400 |
| Asn 785 | Phe | Glu | Lys | Glu | Tyr 790 | Arg | Gln | Leu | Asp | Tyr 795 | Lys | Val | Ile | Ala | Glu 800 | |
| GTA | AAA | ACT | GCG | AAC | GAT | ATA | GCG | AAA | TAT | GAT | GAT | AAA | GGT | TGG | CCA | 2448 |
| Val | Lys | Thr | Ala | Asn 805 | Asp | Ile | Ala | Lys | Tyr 810 | Asp | Asp | Lys | Gly | Trp 815 | Pro | |
| GGA | TTT | AAA | TGT | CCG | TTC | CAT | ATT | CGT | GGT | GTG | CTA | ACT | TAT | CGT | CGA | 2496 |
| Gly | Phe | Lys | Cys 820 | Pro | Phe | His | Ile | Arg 825 | Gly | Val | Leu | Thr | Tyr 830 | Arg | Arg | |
| GCT | GTT | AGT | GGT | CTG | GGT | GTA | GCT | CCA | ATT | TTG | GAT | GGA | AAT | AAA | GTA | 2544 |
| Ala | Val | Ser 835 | Gly | Leu | Gly | Val | Ala 840 | Pro | Ile | Leu | Asp | Gly 845 | Asn | Lys | Val | |
| ATG | GTT | CTT | CCA | TTA | CGT | GAA | GGA | AAT | CCG | TTT | GGT | GAT | AAG | TGC | ATT | 2592 |
| Met | Val 850 | Leu | Pro | Leu | Arg | Glu 855 | Gly | Asn | Pro | Phe | Gly 860 | Asp | Lys | Cys | Ile | |
| GCT | TGG | CCA | TCG | GGT | ACA | GAA | CTT | CCA | AAA | GAA | ATT | CGT | TCT | GAT | GTA | 2640 |
| Ala 865 | Trp | Pro | Ser | Gly | Thr 870 | Glu | Leu | Pro | Lys | Glu 875 | Ile | Arg | Ser | Asp | Val 880 | |
| CTA | TCT | TGG | ATT | GAC | TAC | TCA | ACT | TTG | TTC | CAA | AAA | TCG | TTT | GTT | AAA | 2688 |
| Leu | Ser | Trp | Ile | Asp 885 | Tyr | Ser | Thr | Leu | Phe 890 | Gln | Lys | Ser | Phe | Val 895 | Lys | |
| CCG | CTT | GCG | GGT | ATG | TGT | GAA | TCG | GCA | GGT | ATG | GAC | TAT | GAG | GAA | AAA | 2736 |
| Pro | Leu | Ala | Gly 900 | Met | Cys | Glu | Ser | Ala 905 | Gly | Met | Asp | Tyr | Glu 910 | Glu | Lys | |
| GCT | TCG | TTA | GAC | TTC | CTG | TTT | GGC | | | | | | | | | 2760 |
| Ala | Ser | Leu 915 | Asp | Phe | Leu | Phe | Gly 920 | | | | | | | | | |

( 2 ) INFORMATION FOR SEQ ID NO:2:

( i ) SEQUENCE CHARACTERISTICS:
        ( A ) LENGTH: 920 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

-continued

| | | | | | | | | | | | | | | |
|---|---|---|---|---|---|---|---|---|---|---|---|---|---|---|
| Arg 1 | His | Leu | His | Phe 5 | Phe | Phe | Phe | Phe | Phe 10 | Phe | Phe | Phe | Phe | Phe 15 |
| Phe | Phe | Phe | Phe 20 | Ile | Ile | Met | Lys | Glu 25 | Phe | Tyr | Ile | Ser | Ile 30 | Glu | Thr |
| Val | Gly | Asn 35 | Asn | Ile | Ile | Glu | Arg 40 | Tyr | Ile | Asp | Glu | Asn 45 | Gly | Lys | Glu |
| Arg | Thr 50 | Arg | Glu | Val | Glu | Tyr 55 | Leu | Pro | Thr | Met | Phe 60 | Arg | His | Cys | Lys |
| Glu 65 | Glu | Ser | Lys | Tyr | Lys 70 | Asp | Ile | Tyr | Gly | Lys 75 | Asn | Cys | Ala | Pro | Gln 80 |
| Lys | Phe | Pro | Ser | Met 85 | Lys | Asp | Ala | Arg | Asp 90 | Trp | Met | Lys | Arg | Met 95 | Glu |
| Asp | Ile | Gly | Leu 100 | Glu | Ala | Leu | Gly | Met 105 | Asn | Asp | Phe | Lys | Leu 110 | Ala | Tyr |
| Ile | Ser | Asp | Thr 115 | Tyr | Gly | Ser | Glu 120 | Ile | Val | Tyr | Asp | Arg 125 | Lys | Phe | Val |
| Arg | Val 130 | Ala | Asn | Cys | Asp | Ile 135 | Glu | Val | Thr | Gly | Asp 140 | Lys | Phe | Pro | Asp |
| Pro 145 | Met | Lys | Ala | Glu | Tyr 150 | Glu | Ile | Asp | Ala | Ile 155 | Thr | His | Tyr | Asp | Ser 160 |
| Ile | Asp | Asp | Arg | Phe 165 | Tyr | Val | Phe | Asp | Leu 170 | Leu | Asn | Ser | Met | Tyr 175 | Gly |
| Ser | Val | Ser | Lys 180 | Trp | Asp | Ala | Lys | Leu 185 | Ala | Ala | Lys | Leu | Asp 190 | Cys | Glu |
| Gly | Gly | Asp 195 | Glu | Val | Pro | Gln | Glu 200 | Ile | Leu | Asp | Arg | Val 205 | Ile | Tyr | Met |
| Pro | Phe 210 | Asp | Asn | Glu | Arg | Asp 215 | Met | Leu | Met | Glu | Tyr 220 | Ile | Asn | Leu | Trp |
| Glu 225 | Gln | Lys | Arg | Pro | Ala 230 | Ile | Phe | Thr | Gly | Trp 235 | Asn | Ile | Glu | Gly | Phe 240 |
| Asp | Val | Pro | Tyr | Ile 245 | Met | Asn | Arg | Val | Lys 250 | Met | Ile | Leu | Gly | Glu 255 | Arg |
| Ser | Met | Lys | Arg 260 | Phe | Ser | Pro | Ile | Gly 265 | Arg | Val | Lys | Ser | Lys 270 | Leu | Ile |
| Gln | Asn | Met 275 | Tyr | Gly | Ser | Lys | Glu 280 | Ile | Tyr | Ser | Ile | Asp 285 | Gly | Val | Ser |
| Ile | Leu 290 | Asp | Tyr | Leu | Asp | Leu 295 | Tyr | Lys | Lys | Phe | Ala 300 | Phe | Thr | Asn | Leu |
| Pro 305 | Ser | Phe | Ser | Leu | Glu 310 | Ser | Val | Ala | Gln | His 315 | Glu | Thr | Lys | Lys | Gly 320 |
| Lys | Leu | Pro | Tyr | Asp 325 | Gly | Pro | Ile | Asn | Lys 330 | Leu | Arg | Glu | Thr | Asn 335 | His |
| Gln | Arg | Tyr | Ile 340 | Ser | Tyr | Asn | Ile | Ile 345 | Asp | Val | Glu | Ser | Val 350 | Gln | Ala |
| Ile | Asp | Lys 355 | Ile | Arg | Gly | Phe | Ile 360 | Asp | Leu | Val | Leu | Ser 365 | Met | Ser | Tyr |
| Tyr | Ala 370 | Lys | Met | Pro | Phe | Ser 375 | Gly | Val | Met | Ser | Pro 380 | Ile | Lys | Thr | Trp |
| Asp 385 | Ala | Ile | Ile | Phe | Asn 390 | Ser | Leu | Lys | Gly | Glu 395 | His | Lys | Val | Ile | Pro 400 |
| Gln | Gln | Gly | Ser | His 405 | Val | Lys | Gln | Ser | Phe 410 | Pro | Gly | Ala | Phe | Val 415 | Phe |
| Glu | Pro | Lys | Pro | Ile | Ala | Arg | Arg | Tyr | Ile | Met | Ser | Phe | Asp | Leu | Thr |

|     |     |     |     |     | 420 |     |     |     |     |     | 425 |     |     |     |     |     | 430 |     |     |
| --- | --- | --- | --- | --- | --- | --- | --- | --- | --- | --- | --- | --- | --- | --- | --- | --- | --- | --- | --- |
| Ser | Leu | Tyr 435 | Pro | Ser | Ile | Ile | Arg 440 | Gln | Val | Asn | Ile | Ser 445 | Pro | Glu | Thr |
| Ile | Arg | Gly 450 | Gln | Phe | Lys | Val 455 | His | Pro | Ile | His 460 | Glu | Tyr | Ile | Ala | Gly |
| Thr 465 | Ala | Pro | Lys | Pro | Ser 470 | Asp | Glu | Tyr | Ser | Cys 475 | Ser | Pro | Asn | Gly | Trp 480 |
| Met | Tyr | Asp | Lys | His 485 | Gln | Glu | Gly | Ile | Ile 490 | Pro | Lys | Glu | Ile | Ala | Lys 495 |
| Val | Phe | Phe | Gln | Arg 500 | Lys | Asp | Trp | Lys 505 | Lys | Lys | Met | Phe | Ala 510 | Glu | Glu |
| Met | Asn | Ala 515 | Glu | Ala | Ile | Lys | Lys 520 | Ile | Ile | Met | Lys | Gly 525 | Ala | Gly | Ser |
| Cys | Ser 530 | Thr | Lys | Pro | Glu | Val 535 | Glu | Arg | Tyr | Val | Lys 540 | Phe | Thr | Asp | Asp |
| Phe 545 | Leu | Asn | Glu | Leu | Ser 550 | Asn | Tyr | Thr | Glu | Ser 555 | Val | Leu | Asn | Ser | Leu 560 |
| Ile | Glu | Glu | Cys | Glu 565 | Lys | Ala | Ala | Thr | Leu 570 | Ala | Asn | Thr | Asn | Gln 575 | Leu |
| Asn | Arg | Lys | Ile 580 | Leu | Ile | Asn | Ser | Leu 585 | Tyr | Gly | Ala | Leu | Gly 590 | Asn | Ile |
| His | Phe | Arg 595 | Tyr | Tyr | Asp | Leu | Arg 600 | Asn | Ala | Thr | Ala | Ile 605 | Thr | Ile | Phe |
| Gly | Gln 610 | Val | Gly | Ile | Gln | Trp 615 | Ile | Ala | Arg | Lys | Ile 620 | Asn | Glu | Tyr | Leu |
| Asn 625 | Lys | Val | Cys | Gly | Thr 630 | Asn | Asp | Glu | Asp | Phe 635 | Ile | Ala | Ala | Gly | Asp 640 |
| Thr | Asp | Ser | Val | Tyr 645 | Val | Cys | Val | Asp | Lys 650 | Val | Ile | Glu | Lys | Val 655 | Gly |
| Leu | Asp | Arg | Phe 660 | Lys | Glu | Gln | Asn | Asp 665 | Leu | Val | Glu | Phe | Met 670 | Asn | Gln |
| Phe | Gly | Lys 675 | Lys | Lys | Met | Glu | Pro 680 | Met | Ile | Asp | Val | Ala 685 | Tyr | Arg | Glu |
| Leu | Cys 690 | Asp | Tyr | Met | Asn | Asn 695 | Arg | Glu | His | Leu | Met 700 | His | Met | Asp | Arg |
| Glu 705 | Ala | Ile | Ser | Cys | Pro 710 | Pro | Leu | Gly | Ser | Lys 715 | Gly | Val | Gly | Gly | Phe 720 |
| Trp | Lys | Ala | Lys | Lys 725 | Arg | Tyr | Ala | Leu | Asn 730 | Val | Tyr | Asp | Met | Glu 735 | Asp |
| Lys | Arg | Phe | Ala 740 | Glu | Pro | His | Leu | Lys 745 | Ile | Met | Gly | Met | Glu 750 | Thr | Gln |
| Gln | Ser | Ser 755 | Thr | Pro | Lys | Ala | Val 760 | Gln | Glu | Ala | Leu | Glu 765 | Glu | Ser | Ile |
| Arg | Arg 770 | Ile | Leu | Gln | Glu | Gly 775 | Glu | Glu | Ser | Val | Gln 780 | Glu | Tyr | Tyr | Lys |
| Asn 785 | Phe | Glu | Lys | Glu | Tyr 790 | Arg | Gln | Leu | Asp | Tyr 795 | Lys | Val | Ile | Ala | Glu 800 |
| Val | Lys | Thr | Ala | Asn 805 | Asp | Ile | Ala | Lys | Tyr 810 | Asp | Asp | Lys | Gly | Trp 815 | Pro |
| Gly | Phe | Lys | Cys 820 | Pro | Phe | His | Ile | Arg 825 | Gly | Val | Leu | Thr | Tyr 830 | Arg | Arg |
| Ala | Val | Ser 835 | Gly | Leu | Gly | Val | Ala 840 | Pro | Ile | Leu | Asp | Gly 845 | Asn | Lys | Val |

```
Met  Val  Leu  Pro  Leu  Arg  Glu  Gly  Asn  Pro  Phe  Gly  Asp  Lys  Cys  Ile
     850            855                      860

Ala  Trp  Pro  Ser  Gly  Thr  Glu  Leu  Pro  Lys  Glu  Ile  Arg  Ser  Asp  Val
865                      870                      875                      880

Leu  Ser  Trp  Ile  Asp  Tyr  Ser  Thr  Leu  Phe  Gln  Lys  Ser  Phe  Val  Lys
                    885                      890                      895

Pro  Leu  Ala  Gly  Met  Cys  Glu  Ser  Ala  Gly  Met  Asp  Tyr  Glu  Glu  Lys
               900                      905                      910

Ala  Ser  Leu  Asp  Phe  Leu  Phe  Gly
               915                 920
```

( 2 ) INFORMATION FOR SEQ ID NO:3:

( i ) SEQUENCE CHARACTERISTICS:
        ( A ) LENGTH: 2760 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..2760

( x i ) SEQUENCE DESCRIPTION: SEQ ID NO:3:

```
CGT  CAT  CTT  CAT  TTT  TTT  TTT  TTT  TTT  TTT  TTT  TTT  TTT  TTT  TTT  TTT    48
Arg  His  Leu  His  Phe  Phe  Phe  Phe  Phe  Phe  Phe  Phe  Phe  Phe  Phe  Phe
1                   5                        10                      15

TTT  TTT  TTT  TTT  ATT  ATT  ATG  AAA  GAA  TTT  TAT  ATC  TCT  ATT  GAA  ACA    96
Phe  Phe  Phe  Phe  Ile  Ile  Met  Lys  Glu  Phe  Tyr  Ile  Ser  Ile  Glu  Thr
               20                       25                      30

GTC  GGA  AAT  AAC  ATT  GTT  GAA  CGT  TAT  ATT  GAT  GAA  AAT  GGA  AAG  GAA   144
Val  Gly  Asn  Asn  Ile  Val  Glu  Arg  Tyr  Ile  Asp  Glu  Asn  Gly  Lys  Glu
          35                       40                      45

CGT  ACC  CGT  GAA  GTA  GAA  TAT  CTT  CCA  ACT  ATG  TTT  AGG  CAT  TGT  AAG   192
Arg  Thr  Arg  Glu  Val  Glu  Tyr  Leu  Pro  Thr  Met  Phe  Arg  His  Cys  Lys
     50                       55                      60

GAA  GAG  TCA  AAA  TAC  AAA  GAC  ATC  TAT  GGT  AAA  AAC  TGC  GCT  CCT  CAA   240
Glu  Glu  Ser  Lys  Tyr  Lys  Asp  Ile  Tyr  Gly  Lys  Asn  Cys  Ala  Pro  Gln
65                  70                      75                           80

AAA  TTT  CCA  TCA  ATG  AAA  GAT  GCT  CGA  GAT  TGG  ATG  AAG  CGA  ATG  GAA   288
Lys  Phe  Pro  Ser  Met  Lys  Asp  Ala  Arg  Asp  Trp  Met  Lys  Arg  Met  Glu
               85                       90                      95

GAC  ATC  GGT  CTC  GAA  GCT  CTC  GGT  ATG  AAC  GAT  TTT  AAA  CTC  GCT  TAT   336
Asp  Ile  Gly  Leu  Glu  Ala  Leu  Gly  Met  Asn  Asp  Phe  Lys  Leu  Ala  Tyr
          100                      105                     110

ATA  AGT  GAT  ACA  TAT  GGT  TCA  GAA  ATT  GTT  TAT  GAC  CGA  AAA  TTT  GTT   384
Ile  Ser  Asp  Thr  Tyr  Gly  Ser  Glu  Ile  Val  Tyr  Asp  Arg  Lys  Phe  Val
     115                      120                     125

CGT  GTA  GCT  AAC  TGT  GAC  ATT  GAG  GTT  ACT  GGT  GAT  AAA  TTT  CCT  GAC   432
Arg  Val  Ala  Asn  Cys  Asp  Ile  Glu  Val  Thr  Gly  Asp  Lys  Phe  Pro  Asp
130                      135                     140

CCA  ATG  AAA  GCA  GAA  TAT  GAA  ATT  GAT  GCT  ATC  ACT  CAT  TAC  GAT  TCA   480
Pro  Met  Lys  Ala  Glu  Tyr  Glu  Ile  Asp  Ala  Ile  Thr  His  Tyr  Asp  Ser
145                 150                     155                          160

ATT  GAC  GAT  CGT  TTT  TAT  GTT  TTC  GAC  CTT  TTG  AAT  TCA  ATG  TAC  GGT   528
Ile  Asp  Asp  Arg  Phe  Tyr  Val  Phe  Asp  Leu  Leu  Asn  Ser  Met  Tyr  Gly
               165                     170                     175

TCA  GTA  TCA  AAA  TGG  GAT  GCA  AAG  TTA  GCT  GCT  AAG  CTT  GAC  TGT  GAA   576
Ser  Val  Ser  Lys  Trp  Asp  Ala  Lys  Leu  Ala  Ala  Lys  Leu  Asp  Cys  Glu
          180                     185                     190
```

| | | | | | | | | | | | | | | | | |
|---|---|---|---|---|---|---|---|---|---|---|---|---|---|---|---|---|
| GGT | GGT | GAT | GAA | GTT | CCT | CAA | GAA | ATT | CTT | GAC | CGA | GTA | ATT | TAT | ATG | 624 |
| Gly | Gly | Asp | Glu | Val | Pro | Gln | Glu | Ile | Leu | Asp | Arg | Val | Ile | Tyr | Met | |
| | | 195 | | | | 200 | | | | | 205 | | | | | |
| CCA | TTC | GAT | AAT | GAG | CGT | GAT | ATG | CTC | ATG | GAA | TAT | ATC | AAT | CTT | TGG | 672 |
| Pro | Phe | Asp | Asn | Glu | Arg | Asp | Met | Leu | Met | Glu | Tyr | Ile | Asn | Leu | Trp | |
| | | 210 | | | | 215 | | | | 220 | | | | | | |
| GAA | CAG | AAA | CGA | CCT | GCT | ATT | TTT | ACT | GGT | TGG | AAT | ATT | GAG | GGG | TTT | 720 |
| Glu | Gln | Lys | Arg | Pro | Ala | Ile | Phe | Thr | Gly | Trp | Asn | Ile | Glu | Gly | Phe | |
| 225 | | | | | 230 | | | | | 235 | | | | | 240 | |
| GAC | GTT | CCG | TAT | ATC | ATG | AAT | CGT | GTT | AAA | ATG | ATT | CTG | GGT | GAA | CGT | 768 |
| Asp | Val | Pro | Tyr | Ile | Met | Asn | Arg | Val | Lys | Met | Ile | Leu | Gly | Glu | Arg | |
| | | | | 245 | | | | 250 | | | | | 255 | | | |
| AGT | ATG | AAA | CGT | TTC | TCT | CCA | ATC | GGT | CGG | GTA | AAA | TCT | AAA | CTA | ATT | 816 |
| Ser | Met | Lys | Arg | Phe | Ser | Pro | Ile | Gly | Arg | Val | Lys | Ser | Lys | Leu | Ile | |
| | | | 260 | | | | | 265 | | | | 270 | | | | |
| CAA | AAT | ATG | TAC | GGT | AGC | AAA | GAA | ATT | TAT | TCT | ATT | GAT | GGC | GTA | TCT | 864 |
| Gln | Asn | Met | Tyr | Gly | Ser | Lys | Glu | Ile | Tyr | Ser | Ile | Asp | Gly | Val | Ser | |
| | | 275 | | | | | 280 | | | | | 285 | | | | |
| ATT | CTT | GAT | TAT | TTA | GAT | TTG | TAC | AAG | AAA | TTC | GCT | TTT | ACT | AAT | TTG | 912 |
| Ile | Leu | Asp | Tyr | Leu | Asp | Leu | Tyr | Lys | Lys | Phe | Ala | Phe | Thr | Asn | Leu | |
| | | 290 | | | | 295 | | | | | 300 | | | | | |
| CCG | TCA | TTC | TCT | TTG | GAA | TCA | GTT | GCT | CAA | CAT | GAA | ACC | AAA | AAA | GGT | 960 |
| Pro | Ser | Phe | Ser | Leu | Glu | Ser | Val | Ala | Gln | His | Glu | Thr | Lys | Lys | Gly | |
| 305 | | | | | 310 | | | | | 315 | | | | | 320 | |
| AAA | TTA | CCA | TAC | GAC | GGT | CCT | ATT | AAT | AAA | CTT | CGT | GAG | ACT | AAT | CAT | 1008 |
| Lys | Leu | Pro | Tyr | Asp | Gly | Pro | Ile | Asn | Lys | Leu | Arg | Glu | Thr | Asn | His | |
| | | | | 325 | | | | | 330 | | | | | 335 | | |
| CAA | CGA | TAC | ATT | AGT | TAT | AAC | ATC | ATT | GAC | GTA | GAA | TCA | GTT | CAA | GCA | 1056 |
| Gln | Arg | Tyr | Ile | Ser | Tyr | Asn | Ile | Ile | Asp | Val | Glu | Ser | Val | Gln | Ala | |
| | | | 340 | | | | | 345 | | | | | 350 | | | |
| ATC | GAT | AAA | ATT | CGT | GGG | TTT | ATC | GAT | CTA | GTT | TTA | AGT | ATG | TCT | TAT | 1104 |
| Ile | Asp | Lys | Ile | Arg | Gly | Phe | Ile | Asp | Leu | Val | Leu | Ser | Met | Ser | Tyr | |
| | | 355 | | | | | 360 | | | | | 365 | | | | |
| TAC | GCT | AAA | ATG | CCT | TTT | TCT | GGT | GTA | ATG | AGT | CCT | ATT | AAA | ACT | TGG | 1152 |
| Tyr | Ala | Lys | Met | Pro | Phe | Ser | Gly | Val | Met | Ser | Pro | Ile | Lys | Thr | Trp | |
| | | 370 | | | | 375 | | | | | 380 | | | | | |
| GAT | GCT | ATT | ATT | TTT | AAC | TCA | TTG | AAA | GGT | GAA | CAT | AAG | GTT | ATT | CCT | 1200 |
| Asp | Ala | Ile | Ile | Phe | Asn | Ser | Leu | Lys | Gly | Glu | His | Lys | Val | Ile | Pro | |
| 385 | | | | | 390 | | | | | 395 | | | | | 400 | |
| CAA | CAA | GGT | TCG | CAC | GTT | AAA | CAG | AGT | TTT | CCG | GGT | GCA | TTT | GTG | TTT | 1248 |
| Gln | Gln | Gly | Ser | His | Val | Lys | Gln | Ser | Phe | Pro | Gly | Ala | Phe | Val | Phe | |
| | | | | 405 | | | | | 410 | | | | | 415 | | |
| GAA | CCT | AAA | CCA | ATT | GCA | CGT | CGA | TAC | ATT | ATG | AGT | TTT | GAC | TTG | ACG | 1296 |
| Glu | Pro | Lys | Pro | Ile | Ala | Arg | Arg | Tyr | Ile | Met | Ser | Phe | Asp | Leu | Thr | |
| | | | 420 | | | | | 425 | | | | | 430 | | | |
| TCT | CTG | TAT | CCG | AGC | ATT | ATT | CGC | CAG | GTT | AAC | ATT | AGT | CCT | GAA | ACT | 1344 |
| Ser | Leu | Tyr | Pro | Ser | Ile | Ile | Arg | Gln | Val | Asn | Ile | Ser | Pro | Glu | Thr | |
| | | 435 | | | | | 440 | | | | | 445 | | | | |
| ATT | CGT | GGT | CAG | TTT | AAA | GTT | CAT | CCA | ATT | CAT | GAA | TAT | ATC | GCA | GGA | 1392 |
| Ile | Arg | Gly | Gln | Phe | Lys | Val | His | Pro | Ile | His | Glu | Tyr | Ile | Ala | Gly | |
| | | 450 | | | | | 455 | | | | | 460 | | | | |
| ACA | GCT | CCT | AAA | CCG | AGT | GAT | GAA | TAT | TCT | TGT | TCT | CCG | AAT | GGA | TGG | 1440 |
| Thr | Ala | Pro | Lys | Pro | Ser | Asp | Glu | Tyr | Ser | Cys | Ser | Pro | Asn | Gly | Trp | |
| 465 | | | | | 470 | | | | | 475 | | | | | 480 | |
| ATG | TAT | GAT | AAA | CAT | CAA | GAA | GGT | ATC | ATT | CCA | AAG | GAA | ATC | GCT | AAA | 1488 |
| Met | Tyr | Asp | Lys | His | Gln | Glu | Gly | Ile | Ile | Pro | Lys | Glu | Ile | Ala | Lys | |
| | | | | 485 | | | | | 490 | | | | | 495 | | |
| GTA | TTT | TTC | CAG | CGT | AAA | GAC | TGG | AAA | AAG | AAA | ATG | TTC | GCT | GAA | GAA | 1536 |
| Val | Phe | Phe | Gln | Arg | Lys | Asp | Trp | Lys | Lys | Lys | Met | Phe | Ala | Glu | Glu | |
| | | | 500 | | | | | 505 | | | | | 510 | | | |

| | | | | | | | | | | | | | | | | |
|---|---|---|---|---|---|---|---|---|---|---|---|---|---|---|---|---|
| ATG | AAT | GCC | GAA | GCT | ATT | AAA | AAG | ATT | ATT | ATG | AAA | GGC | GCA | GGG | TCT | 1584 |
| Met | Asn | Ala | Glu | Ala | Ile | Lys | Lys | Ile | Ile | Met | Lys | Gly | Ala | Gly | Ser | |
| | | 515 | | | | 520 | | | | | 525 | | | | | |
| TGT | TCA | ACT | AAA | CCA | GAA | GTT | GAA | CGA | TAT | GTT | AAG | TTC | AGT | GAT | GAT | 1632 |
| Cys | Ser | Thr | Lys | Pro | Glu | Val | Glu | Arg | Tyr | Val | Lys | Phe | Ser | Asp | Asp | |
| | 530 | | | | | 535 | | | | | 540 | | | | | |
| TTC | TTA | AAT | GAA | CTA | TCG | AAT | TAC | ACC | GAA | TCT | GTT | CTC | AAT | AGT | CTG | 1680 |
| Phe | Leu | Asn | Glu | Leu | Ser | Asn | Tyr | Thr | Glu | Ser | Val | Leu | Asn | Ser | Leu | |
| 545 | | | | | 550 | | | | | 555 | | | | | 560 | |
| ATT | GAA | GAA | TGT | GAA | AAA | GCA | GCT | ACA | CTT | GCT | AAT | ACA | AAT | CAG | CTG | 1728 |
| Ile | Glu | Glu | Cys | Glu | Lys | Ala | Ala | Thr | Leu | Ala | Asn | Thr | Asn | Gln | Leu | |
| | | | | 565 | | | | | 570 | | | | | 575 | | |
| AAC | CGT | AAA | ATT | CTC | ATT | AAC | AGT | CTT | TAT | GGT | GCT | CTT | GGT | AAT | ATT | 1776 |
| Asn | Arg | Lys | Ile | Leu | Ile | Asn | Ser | Leu | Tyr | Gly | Ala | Leu | Gly | Asn | Ile | |
| | | | 580 | | | | | 585 | | | | | 590 | | | |
| CAT | TTC | CGT | TAC | TAT | GAT | TTG | CGA | AAT | GCT | ACT | GCT | ATC | ACA | ATT | TTC | 1824 |
| His | Phe | Arg | Tyr | Tyr | Asp | Leu | Arg | Asn | Ala | Thr | Ala | Ile | Thr | Ile | Phe | |
| | | 595 | | | | | 600 | | | | | 605 | | | | |
| GGC | CAA | GTC | GGT | ATT | CAG | TGG | ATT | GCT | CGT | AAA | ATT | AAT | GAA | TAT | CTG | 1872 |
| Gly | Gln | Val | Gly | Ile | Gln | Trp | Ile | Ala | Arg | Lys | Ile | Asn | Glu | Tyr | Leu | |
| | 610 | | | | | 615 | | | | | 620 | | | | | |
| AAT | AAA | GTA | TGC | GGA | ACT | AAT | GAT | GAA | GAT | TTC | ATT | GCA | GCA | GGT | GAT | 1920 |
| Asn | Lys | Val | Cys | Gly | Thr | Asn | Asp | Glu | Asp | Phe | Ile | Ala | Ala | Gly | Asp | |
| 625 | | | | | 630 | | | | | 635 | | | | | 640 | |
| ACT | GAT | TCG | GTA | TAT | GTT | TGC | GTA | GAT | AAA | GTT | ATT | GAA | AAA | GTT | GGT | 1968 |
| Thr | Asp | Ser | Val | Tyr | Val | Cys | Val | Asp | Lys | Val | Ile | Glu | Lys | Val | Gly | |
| | | | | 645 | | | | | 650 | | | | | 655 | | |
| CTT | GAC | CGA | TTC | AAA | GAG | CAG | AAC | GAT | TTG | GTT | GAA | TTC | ATG | AAT | CAG | 2016 |
| Leu | Asp | Arg | Phe | Lys | Glu | Gln | Asn | Asp | Leu | Val | Glu | Phe | Met | Asn | Gln | |
| | | | 660 | | | | | 665 | | | | | 670 | | | |
| TTC | GGT | AAG | AAA | AAG | ATG | GAA | CCT | ATG | ATT | GAT | GTT | GCA | TAT | CGT | GAG | 2064 |
| Phe | Gly | Lys | Lys | Lys | Met | Glu | Pro | Met | Ile | Asp | Val | Ala | Tyr | Arg | Glu | |
| | | 675 | | | | | 680 | | | | | 685 | | | | |
| TTA | TGT | GAT | TAT | ATG | AAT | AAC | CGC | GAG | CAT | CTG | ATG | CAT | ATG | GAC | CGT | 2112 |
| Leu | Cys | Asp | Tyr | Met | Asn | Asn | Arg | Glu | His | Leu | Met | His | Met | Asp | Arg | |
| | 690 | | | | | 695 | | | | | 700 | | | | | |
| GAA | GCT | ATT | TCT | TGC | CCT | CCG | CTT | GGT | TCA | AAG | GGC | GTT | GGT | GGA | TTT | 2160 |
| Glu | Ala | Ile | Ser | Cys | Pro | Pro | Leu | Gly | Ser | Lys | Gly | Val | Gly | Gly | Phe | |
| 705 | | | | | 710 | | | | | 715 | | | | | 720 | |
| TGG | AAA | GCG | AAA | AAG | CGT | TAT | GCT | CTG | AAC | GTT | TAT | GAT | ATG | GAA | GAT | 2208 |
| Trp | Lys | Ala | Lys | Lys | Arg | Tyr | Ala | Leu | Asn | Val | Tyr | Asp | Met | Glu | Asp | |
| | | | | 725 | | | | | 730 | | | | | 735 | | |
| AAG | CGA | TTT | GCT | GAA | CCG | CAT | CTA | AAA | ATC | ATG | GGT | ATG | GAA | ACT | CAG | 2256 |
| Lys | Arg | Phe | Ala | Glu | Pro | His | Leu | Lys | Ile | Met | Gly | Met | Glu | Thr | Gln | |
| | | | 740 | | | | | 745 | | | | | 750 | | | |
| CAG | AGT | TCA | ACA | CCA | AAA | GCA | GTG | CAA | GAA | GCT | CTC | GAA | GAA | AGT | ATT | 2304 |
| Gln | Ser | Ser | Thr | Pro | Lys | Ala | Val | Gln | Glu | Ala | Leu | Glu | Glu | Ser | Ile | |
| | | 755 | | | | | 760 | | | | | 765 | | | | |
| CGT | CGT | ATT | CTT | CAG | GAA | GGT | GAA | GAG | TCT | GTC | CAA | GAA | TAC | TAC | AAG | 2352 |
| Arg | Arg | Ile | Leu | Gln | Glu | Gly | Glu | Glu | Ser | Val | Gln | Glu | Tyr | Tyr | Lys | |
| | 770 | | | | | 775 | | | | | 780 | | | | | |
| AAC | TTC | GAG | AAA | GAA | TAT | CGT | CAA | CTT | GAC | TAT | AAA | GTT | ATT | GCT | GAA | 2400 |
| Asn | Phe | Glu | Lys | Glu | Tyr | Arg | Gln | Leu | Asp | Tyr | Lys | Val | Ile | Ala | Glu | |
| 785 | | | | | 790 | | | | | 795 | | | | | 800 | |
| GTA | AAA | ACT | GCG | AAC | GAT | ATA | GCG | AAA | TAT | GAT | GAT | AAA | GGT | TGG | CCA | 2448 |
| Val | Lys | Thr | Ala | Asn | Asp | Ile | Ala | Lys | Tyr | Asp | Asp | Lys | Gly | Trp | Pro | |
| | | | | 805 | | | | | 810 | | | | | 815 | | |
| GGA | TTT | AAA | TGC | CCG | TTC | CAT | ATT | CGT | GGT | GTG | CTA | ACT | TAT | CGT | CGA | 2496 |
| Gly | Phe | Lys | Cys | Pro | Phe | His | Ile | Arg | Gly | Val | Leu | Thr | Tyr | Arg | Arg | |
| | | | 820 | | | | | 825 | | | | | 830 | | | |

```
GCT GTT AGC GGT TTA GGT GTA GCT CCA ATT TTG GAT GGA AAT AAA GTA       2544
Ala Val Ser Gly Leu Gly Val Ala Pro Ile Leu Asp Gly Asn Lys Val
        835                 840                 845

ATG GTT CTT CCA TTA CGT GAA GGA AAT CCA TTT GGT GAC AAG TGC ATT       2592
Met Val Leu Pro Leu Arg Glu Gly Asn Pro Phe Gly Asp Lys Cys Ile
850                     855                 860

GCT TGG CCA TCG GGT ACA GAA CTT CCA AAA GAA ATT CGT TCT GAT GTG       2640
Ala Trp Pro Ser Gly Thr Glu Leu Pro Lys Glu Ile Arg Ser Asp Val
865                     870                 875                 880

CTA TCT TGG ATT GAC CAC TCA ACT TTG TTC CAA AAA TCG TTT GTT AAA       2688
Leu Ser Trp Ile Asp His Ser Thr Leu Phe Gln Lys Ser Phe Val Lys
                    885                 890                 895

CCG CTT GCG GGT ATG TGT GAA TCG GCT GGC ATG GAC TAT GAA GAA AAA       2736
Pro Leu Ala Gly Met Cys Glu Ser Ala Gly Met Asp Tyr Glu Glu Lys
            900                 905                 910

GCT TCG TTA GAC TTC CTG TTT GGC                                       2760
Ala Ser Leu Asp Phe Leu Phe Gly
            915                 920
```

( 2 ) INFORMATION FOR SEQ ID NO:4:

( i ) SEQUENCE CHARACTERISTICS:
        ( A ) LENGTH: 920 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Arg His Leu His Phe Phe Phe Phe Phe Phe Phe Phe Phe Phe Phe Phe
 1               5                   10                  15

Phe Phe Phe Phe Ile Ile Met Lys Glu Phe Tyr Ile Ser Ile Glu Thr
            20                  25                  30

Val Gly Asn Asn Ile Val Glu Arg Tyr Ile Asp Glu Asn Gly Lys Glu
            35                  40                  45

Arg Thr Arg Glu Val Glu Tyr Leu Pro Thr Met Phe Arg His Cys Lys
        50                  55                  60

Glu Glu Ser Lys Tyr Lys Asp Ile Tyr Gly Lys Asn Cys Ala Pro Gln
65                  70                  75                  80

Lys Phe Pro Ser Met Lys Asp Ala Arg Asp Trp Met Lys Arg Met Glu
                85                  90                  95

Asp Ile Gly Leu Glu Ala Leu Gly Met Asn Asp Phe Lys Leu Ala Tyr
            100                 105                 110

Ile Ser Asp Thr Tyr Gly Ser Glu Ile Val Tyr Asp Arg Lys Phe Val
            115                 120                 125

Arg Val Ala Asn Cys Asp Ile Glu Val Thr Gly Asp Lys Phe Pro Asp
        130                 135                 140

Pro Met Lys Ala Glu Tyr Glu Ile Asp Ala Ile Thr His Tyr Asp Ser
145                 150                 155                 160

Ile Asp Asp Arg Phe Tyr Val Phe Asp Leu Leu Asn Ser Met Tyr Gly
                165                 170                 175

Ser Val Ser Lys Trp Asp Ala Lys Leu Ala Ala Lys Leu Asp Cys Glu
            180                 185                 190

Gly Gly Asp Glu Val Pro Gln Glu Ile Leu Asp Arg Val Ile Tyr Met
            195                 200                 205

Pro Phe Asp Asn Glu Arg Asp Met Leu Met Glu Tyr Ile Asn Leu Trp
        210                 215                 220

Glu Gln Lys Arg Pro Ala Ile Phe Thr Gly Trp Asn Ile Glu Gly Phe
225                 230                 235                 240
```

```
Asp  Val  Pro  Tyr  Ile  Met  Asn  Arg  Val  Lys  Met  Ile  Leu  Gly  Glu  Arg
               245                 250                      255

Ser  Met  Lys  Arg  Phe  Ser  Pro  Ile  Gly  Arg  Val  Lys  Ser  Lys  Leu  Ile
               260                 265                      270

Gln  Asn  Met  Tyr  Gly  Ser  Lys  Glu  Ile  Tyr  Ser  Ile  Asp  Gly  Val  Ser
          275                      280                 285

Ile  Leu  Asp  Tyr  Leu  Asp  Leu  Tyr  Lys  Lys  Phe  Ala  Phe  Thr  Asn  Leu
          290                 295                      300

Pro  Ser  Phe  Ser  Leu  Glu  Ser  Val  Ala  Gln  His  Glu  Thr  Lys  Lys  Gly
305                      310                 315                           320

Lys  Leu  Pro  Tyr  Asp  Gly  Pro  Ile  Asn  Lys  Leu  Arg  Glu  Thr  Asn  His
               325                 330                      335

Gln  Arg  Tyr  Ile  Ser  Tyr  Asn  Ile  Ile  Asp  Val  Glu  Ser  Val  Gln  Ala
               340                 345                      350

Ile  Asp  Lys  Ile  Arg  Gly  Phe  Ile  Asp  Leu  Val  Leu  Ser  Met  Ser  Tyr
               355                 360                      365

Tyr  Ala  Lys  Met  Pro  Phe  Ser  Gly  Val  Met  Ser  Pro  Ile  Lys  Thr  Trp
          370                 375                      380

Asp  Ala  Ile  Ile  Phe  Asn  Ser  Leu  Lys  Gly  Glu  His  Lys  Val  Ile  Pro
385                      390                 395                           400

Gln  Gln  Gly  Ser  His  Val  Lys  Gln  Ser  Phe  Pro  Gly  Ala  Phe  Val  Phe
               405                 410                      415

Glu  Pro  Lys  Pro  Ile  Ala  Arg  Arg  Tyr  Ile  Met  Ser  Phe  Asp  Leu  Thr
               420                 425                      430

Ser  Leu  Tyr  Pro  Ser  Ile  Ile  Arg  Gln  Val  Asn  Ile  Ser  Pro  Glu  Thr
          435                      440                 445

Ile  Arg  Gly  Gln  Phe  Lys  Val  His  Pro  Ile  His  Glu  Tyr  Ile  Ala  Gly
          450                      455                 460

Thr  Ala  Pro  Lys  Pro  Ser  Asp  Glu  Tyr  Ser  Cys  Ser  Pro  Asn  Gly  Trp
465                      470                 475                           480

Met  Tyr  Asp  Lys  His  Gln  Glu  Gly  Ile  Ile  Pro  Lys  Glu  Ile  Ala  Lys
               485                 490                      495

Val  Phe  Phe  Gln  Arg  Lys  Asp  Trp  Lys  Lys  Met  Phe  Ala  Glu  Glu
               500                 505                      510

Met  Asn  Ala  Glu  Ala  Ile  Lys  Lys  Ile  Ile  Met  Lys  Gly  Ala  Gly  Ser
          515                      520                 525

Cys  Ser  Thr  Lys  Pro  Glu  Val  Glu  Arg  Tyr  Val  Lys  Phe  Ser  Asp  Asp
          530                      535                 540

Phe  Leu  Asn  Glu  Leu  Ser  Asn  Tyr  Thr  Glu  Ser  Val  Leu  Asn  Ser  Leu
545                      550                 555                           560

Ile  Glu  Glu  Cys  Glu  Lys  Ala  Ala  Thr  Leu  Ala  Asn  Thr  Asn  Gln  Leu
               565                 570                      575

Asn  Arg  Lys  Ile  Leu  Ile  Asn  Ser  Leu  Tyr  Gly  Ala  Leu  Gly  Asn  Ile
               580                 585                      590

His  Phe  Arg  Tyr  Tyr  Asp  Leu  Arg  Asn  Ala  Thr  Ala  Ile  Thr  Ile  Phe
          595                      600                 605

Gly  Gln  Val  Gly  Ile  Gln  Trp  Ile  Ala  Arg  Lys  Ile  Asn  Glu  Tyr  Leu
          610                      615                 620

Asn  Lys  Val  Cys  Gly  Thr  Asn  Asp  Glu  Asp  Phe  Ile  Ala  Ala  Gly  Asp
625                      630                 635                           640

Thr  Asp  Ser  Val  Tyr  Val  Cys  Val  Asp  Lys  Val  Ile  Glu  Lys  Val  Gly
               645                 650                      655

Leu  Asp  Arg  Phe  Lys  Glu  Gln  Asn  Asp  Leu  Val  Glu  Phe  Met  Asn  Gln
```

|     |     |     |     |     | 660 |     |     |     |     | 665 |     |     |     |     | 670 |     |     |
| --- | --- | --- | --- | --- | --- | --- | --- | --- | --- | --- | --- | --- | --- | --- | --- | --- | --- |
| Phe | Gly | Lys | Lys | Lys | Met | Glu | Pro | Met | Ile | Asp | Val | Ala | Tyr | Arg | Glu |
|     |     | 675 |     |     |     | 680 |     |     |     |     |     | 685 |     |     |     |
| Leu | Cys | Asp | Tyr | Met | Asn | Asn | Arg | Glu | His | Leu | Met | His | Met | Asp | Arg |
|     |     | 690 |     |     |     | 695 |     |     |     |     | 700 |     |     |     |     |
| Glu | Ala | Ile | Ser | Cys | Pro | Pro | Leu | Gly | Ser | Lys | Gly | Val | Gly | Gly | Phe |
| 705 |     |     |     |     | 710 |     |     |     |     | 715 |     |     |     |     | 720 |
| Trp | Lys | Ala | Lys | Lys | Arg | Tyr | Ala | Leu | Asn | Val | Tyr | Asp | Met | Glu | Asp |
|     |     |     |     | 725 |     |     |     |     | 730 |     |     |     |     | 735 |     |
| Lys | Arg | Phe | Ala | Glu | Pro | His | Leu | Lys | Ile | Met | Gly | Met | Glu | Thr | Gln |
|     |     |     | 740 |     |     |     |     | 745 |     |     |     |     | 750 |     |     |
| Gln | Ser | Ser | Thr | Pro | Lys | Ala | Val | Gln | Glu | Ala | Leu | Glu | Glu | Ser | Ile |
|     |     | 755 |     |     |     |     | 760 |     |     |     |     | 765 |     |     |     |
| Arg | Arg | Ile | Leu | Gln | Glu | Gly | Glu | Glu | Ser | Val | Gln | Glu | Tyr | Tyr | Lys |
|     | 770 |     |     |     |     | 775 |     |     |     |     | 780 |     |     |     |     |
| Asn | Phe | Glu | Lys | Glu | Tyr | Arg | Gln | Leu | Asp | Tyr | Lys | Val | Ile | Ala | Glu |
| 785 |     |     |     |     | 790 |     |     |     |     | 795 |     |     |     |     | 800 |
| Val | Lys | Thr | Ala | Asn | Asp | Ile | Ala | Lys | Tyr | Asp | Asp | Lys | Gly | Trp | Pro |
|     |     |     |     | 805 |     |     |     |     | 810 |     |     |     |     | 815 |     |
| Gly | Phe | Lys | Cys | Pro | Phe | His | Ile | Arg | Gly | Val | Leu | Thr | Tyr | Arg | Arg |
|     |     |     | 820 |     |     |     |     | 825 |     |     |     |     | 830 |     |     |
| Ala | Val | Ser | Gly | Leu | Gly | Val | Ala | Pro | Ile | Leu | Asp | Gly | Asn | Lys | Val |
|     |     | 835 |     |     |     |     | 840 |     |     |     |     | 845 |     |     |     |
| Met | Val | Leu | Pro | Leu | Arg | Glu | Gly | Asn | Pro | Phe | Gly | Asp | Lys | Cys | Ile |
|     | 850 |     |     |     |     | 855 |     |     |     |     | 860 |     |     |     |     |
| Ala | Trp | Pro | Ser | Gly | Thr | Glu | Leu | Pro | Lys | Glu | Ile | Arg | Ser | Asp | Val |
| 865 |     |     |     |     | 870 |     |     |     |     | 875 |     |     |     |     | 880 |
| Leu | Ser | Trp | Ile | Asp | His | Ser | Thr | Leu | Phe | Gln | Lys | Ser | Phe | Val | Lys |
|     |     |     |     | 885 |     |     |     |     | 890 |     |     |     |     | 895 |     |
| Pro | Leu | Ala | Gly | Met | Cys | Glu | Ser | Ala | Gly | Met | Asp | Tyr | Glu | Glu | Lys |
|     |     |     | 900 |     |     |     |     | 905 |     |     |     |     | 910 |     |     |
| Ala | Ser | Leu | Asp | Phe | Leu | Phe | Gly |
|     |     | 915 |     |     |     |     | 920 |

( 2 ) INFORMATION FOR SEQ ID NO:5:

( i ) SEQUENCE CHARACTERISTICS:
        ( A ) LENGTH: 2459 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 108..2456

( x i ) SEQUENCE DESCRIPTION: SEQ ID NO:5:

| AAGCATGGCG | CGAAGGCATA | TTACGGGCAG | TAATGACTGT | ATAAAACCAC | AGCCAATCAA | 60 |
| --- | --- | --- | --- | --- | --- | --- |
| ACGAAACCAG | GCTATACTCA | AGCCTGGTTT | TTTGATGGAT | TTTCAGC | GTG GCG CAG | 116 |
|            |            |            |            |         | Val Ala Gln |     |
|            |            |            |            |         | 1           |     |

| GCA | GGT | TTT | ATC | TTA | ACC | CGA | CAC | TGG | CGG | GAC | ACC | CCG | CAA | GGG | ACA | 164 |
| --- | --- | --- | --- | --- | --- | --- | --- | --- | --- | --- | --- | --- | --- | --- | --- | --- |
| Ala | Gly | Phe | Ile | Leu | Thr | Arg | His | Trp | Arg | Asp | Thr | Pro | Gln | Gly | Thr |     |
|     | 5   |     |     |     |     | 10  |     |     |     |     | 15  |     |     |     |     |     |

| GAA | GTC | TCC | TTC | TGG | CTG | GCG | ACG | GAC | AAC | GGG | CCG | TTG | CAG | GTT | ACG | 212 |
| --- | --- | --- | --- | --- | --- | --- | --- | --- | --- | --- | --- | --- | --- | --- | --- | --- |
| Glu | Val | Ser | Phe | Trp | Leu | Ala | Thr | Asp | Asn | Gly | Pro | Leu | Gln | Val | Thr |     |
| 20  |     |     |     |     | 25  |     |     |     |     | 30  |     |     |     |     | 35  |     |

| | | | | | | | | | | | | | | | | |
|---|---|---|---|---|---|---|---|---|---|---|---|---|---|---|---|---|
| CTT | GCA | CCG | CAA | GAG | TCC | GTG | GCG | TTT | ATT | CCC | GCC | GAT | CAG | GTT | CCC | 260 |
| Leu | Ala | Pro | Gln | Glu | Ser | Val | Ala | Phe | Ile | Pro | Ala | Asp | Gln | Val | Pro | |
| | | | 40 | | | | | 45 | | | | | 50 | | | |
| CGC | GCT | CAG | CAT | ATT | TTG | CAG | GGT | GAA | CAA | GGC | TTT | CGC | CTG | ACA | CCG | 308 |
| Arg | Ala | Gln | His | Ile | Leu | Gln | Gly | Glu | Gln | Gly | Phe | Arg | Leu | Thr | Pro | |
| | | | 55 | | | | 60 | | | | | 65 | | | | |
| CTG | GCG | TTA | AAG | GAT | TTT | CAC | CGC | CAG | CCG | GTG | TAT | GGC | CTT | TAC | TGT | 356 |
| Leu | Ala | Leu | Lys | Asp | Phe | His | Arg | Gln | Pro | Val | Tyr | Gly | Leu | Tyr | Cys | |
| | | 70 | | | | | 75 | | | | | 80 | | | | |
| CGC | GCC | CAT | CGC | CAA | TTG | ATG | AAT | TAC | GAA | AAG | CGC | CTG | CGT | GAA | GGT | 404 |
| Arg | Ala | His | Arg | Gln | Leu | Met | Asn | Tyr | Glu | Lys | Arg | Leu | Arg | Glu | Gly | |
| | 85 | | | | | 90 | | | | | 95 | | | | | |
| GGC | GTT | ACC | GTC | TAC | GAG | GCC | GAT | GTG | CGT | CCG | CCA | GAA | CGC | TAT | CTG | 452 |
| Gly | Val | Thr | Val | Tyr | Glu | Ala | Asp | Val | Arg | Pro | Pro | Glu | Arg | Tyr | Leu | |
| 100 | | | | | 105 | | | | | 110 | | | | | 115 | |
| ATG | GAG | CGG | TTT | ATC | ACC | TCA | CCG | GTG | TGG | GTC | GAG | GGT | GAT | ATG | CAC | 500 |
| Met | Glu | Arg | Phe | Ile | Thr | Ser | Pro | Val | Trp | Val | Glu | Gly | Asp | Met | His | |
| | | | | 120 | | | | | 125 | | | | | 130 | | |
| AAT | GGC | ACT | ATC | GTT | AAT | GCC | CGT | CTG | AAA | CCG | CAT | CCC | GAC | TAT | CGT | 548 |
| Asn | Gly | Thr | Ile | Val | Asn | Ala | Arg | Leu | Lys | Pro | His | Pro | Asp | Tyr | Arg | |
| | | | 135 | | | | | 140 | | | | | 145 | | | |
| CCG | CCG | CTC | AAG | TGG | GTT | TCT | ATA | GAT | ATT | GAA | ACC | ACC | CGC | CAC | GGT | 596 |
| Pro | Pro | Leu | Lys | Trp | Val | Ser | Ile | Asp | Ile | Glu | Thr | Thr | Arg | His | Gly | |
| | | 150 | | | | | 155 | | | | | 160 | | | | |
| GAG | CTG | TAC | TGC | ATC | GGC | CTG | GAA | GGC | TGC | GGG | CAG | CGC | ATC | GTT | TAT | 644 |
| Glu | Leu | Tyr | Cys | Ile | Gly | Leu | Glu | Gly | Cys | Gly | Gln | Arg | Ile | Val | Tyr | |
| | 165 | | | | | 170 | | | | | 175 | | | | | |
| ATG | CTG | GGG | CCG | GAG | AAT | GGC | GAC | GCC | TCC | TCG | CTT | GAT | TTC | GAA | CTG | 692 |
| Met | Leu | Gly | Pro | Glu | Asn | Gly | Asp | Ala | Ser | Ser | Leu | Asp | Phe | Glu | Leu | |
| 180 | | | | | 185 | | | | | 190 | | | | | 195 | |
| GAA | TAC | GTC | GCC | AGC | CGC | CCG | CAG | TTG | CTG | GAA | AAA | CTC | AAC | GCC | TGG | 740 |
| Glu | Tyr | Val | Ala | Ser | Arg | Pro | Gln | Leu | Leu | Glu | Lys | Leu | Asn | Ala | Trp | |
| | | | | 200 | | | | | 205 | | | | | 210 | | |
| TTT | GCC | AAC | TAC | GAT | CCT | GAT | GTG | ATC | ATC | GGT | TGG | AAC | GTG | GTG | CAG | 788 |
| Phe | Ala | Asn | Tyr | Asp | Pro | Asp | Val | Ile | Ile | Gly | Trp | Asn | Val | Val | Gln | |
| | | | 215 | | | | | 220 | | | | | 225 | | | |
| TTC | GAT | CTG | CGA | ATG | CTG | CAA | AAA | CAT | GCC | GAG | CGT | TAC | CGT | CTT | CCG | 836 |
| Phe | Asp | Leu | Arg | Met | Leu | Gln | Lys | His | Ala | Glu | Arg | Tyr | Arg | Leu | Pro | |
| | | 230 | | | | | 235 | | | | | 240 | | | | |
| CTG | CGT | CTT | GGG | CGC | GAT | AAT | AGC | GAG | CTG | GAG | TGG | CGC | GAC | GAC | GGC | 884 |
| Leu | Arg | Leu | Gly | Arg | Asp | Asn | Ser | Glu | Leu | Glu | Trp | Arg | Asp | Asp | Gly | |
| | 245 | | | | | 250 | | | | | 255 | | | | | |
| TTT | AAA | AAC | GGC | GTC | TTT | TTT | GCC | CAG | GCT | AAA | GGT | GGG | CTA | ATT | ATC | 932 |
| Phe | Lys | Asn | Gly | Val | Phe | Phe | Ala | Gln | Ala | Lys | Gly | Gly | Leu | Ile | Ile | |
| 260 | | | | | 265 | | | | | 270 | | | | | 275 | |
| GAC | GGT | ATC | GAG | GCG | CTG | AAA | TCC | GCG | TTC | TGG | AAT | TTC | TCT | TCA | TTC | 980 |
| Asp | Gly | Ile | Glu | Ala | Leu | Lys | Ser | Ala | Phe | Trp | Asn | Phe | Ser | Ser | Phe | |
| | | | | 280 | | | | | 285 | | | | | 290 | | |
| TCG | CTG | GAA | ACT | GTC | GCT | CAG | GAG | CTA | TTA | GGC | GAA | GGA | AAA | TCT | ATC | 1028 |
| Ser | Leu | Glu | Thr | Val | Ala | Gln | Glu | Leu | Leu | Gly | Glu | Gly | Lys | Ser | Ile | |
| | | | | 295 | | | | | 300 | | | | | 305 | | |
| GAT | AAC | CCG | TGG | GAT | CGA | ATG | GAC | GAA | ATT | GAC | CGC | CGT | TTC | GCC | GAA | 1076 |
| Asp | Asn | Pro | Trp | Asp | Arg | Met | Asp | Glu | Ile | Asp | Arg | Arg | Phe | Ala | Glu | |
| | | 310 | | | | | 315 | | | | | 320 | | | | |
| GAT | AAA | CCT | GCG | CTG | GCA | ACT | TAT | AAC | CTG | AAA | GAT | TGC | GAG | CTG | GTG | 1124 |
| Asp | Lys | Pro | Ala | Leu | Ala | Thr | Tyr | Asn | Leu | Lys | Asp | Cys | Glu | Leu | Val | |
| | 325 | | | | | 330 | | | | | 335 | | | | | |
| ACG | CAG | ATC | TTC | CAC | AAA | ACT | GAA | ATC | ATG | CCA | TTT | TTA | CTC | GAA | CGG | 1172 |
| Thr | Gln | Ile | Phe | His | Lys | Thr | Glu | Ile | Met | Pro | Phe | Leu | Leu | Glu | Arg | |
| 340 | | | | | 345 | | | | | 350 | | | | | 355 | |

| | | | | | | | | | | | | | | | | |
|---|---|---|---|---|---|---|---|---|---|---|---|---|---|---|---|---|
| GCA | ACG | GTG | AAC | GGC | CTG | CCG | GTG | GAC | CGA | CAC | GGC | GGT | TCG | GTG | GCG | 1220 |
| Ala | Thr | Val | Asn | Gly 360 | Leu | Pro | Val | Asp | Arg 365 | His | Gly | Gly | Ser | Val 370 | Ala | |
| GCA | TTT | GGT | CAT | CTC | TAT | TTT | CCG | CGA | ATG | CAT | CGC | GCT | GGT | TAT | GTC | 1268 |
| Ala | Phe | Gly | His 375 | Leu | Tyr | Phe | Pro | Arg 380 | Met | His | Arg | Ala | Gly 385 | Tyr | Val | |
| GCG | CCT | AAT | CTC | GGC | GAA | GTG | CCG | CCG | CAC | GCC | AGC | CCT | GGC | GGC | TAC | 1316 |
| Ala | Pro | Asn 390 | Leu | Gly | Glu | Val | Pro 395 | Pro | His | Ala | Ser | Pro 400 | Gly | Gly | Tyr | |
| GTG | ATG | GAT | TCA | CGG | CCA | GGG | CTT | TAT | GAT | TCA | GTG | CTG | GTG | CTG | GAC | 1364 |
| Val | Met 405 | Asp | Ser | Arg | Pro | Gly 410 | Leu | Tyr | Asp | Ser | Val 415 | Leu | Val | Leu | Asp | |
| TAT | AAA | AGC | CTG | TAC | CCG | TCG | ATC | ATC | CGC | ACC | TTT | CTG | ATT | GAT | CCC | 1412 |
| Tyr 420 | Lys | Ser | Leu | Tyr | Pro 425 | Ser | Ile | Ile | Arg | Thr 430 | Phe | Leu | Ile | Asp | Pro 435 | |
| GTC | GGG | CTG | GTG | GAA | GGC | ATG | GCG | CAG | CCT | GAT | CCA | GAG | CAC | AGT | ACC | 1460 |
| Val | Gly | Leu | Val | Glu 440 | Gly | Met | Ala | Gln | Pro 445 | Asp | Pro | Glu | His | Ser 450 | Thr | |
| GAA | GGT | TTT | CTC | GAT | GCC | TGG | TTC | TCG | CGA | GAA | AAA | CAT | TGC | CTG | CCG | 1508 |
| Glu | Gly | Phe | Leu 455 | Asp | Ala | Trp | Phe | Ser 460 | Arg | Glu | Lys | His | Cys 465 | Leu | Pro | |
| GAG | ATT | GTG | ACT | AAC | ATC | TGG | CAC | GGG | CGC | GAT | GAA | GCC | AAA | CGC | CAG | 1556 |
| Glu | Ile | Val 470 | Thr | Asn | Ile | Trp | His 475 | Gly | Arg | Asp | Glu | Ala 480 | Lys | Arg | Gln | |
| GGT | AAC | AAA | CCG | CTG | TCG | CAG | GCG | CTG | AAA | ATC | ATC | ATG | AAT | GCC | TTT | 1604 |
| Gly | Asn | Lys 485 | Pro | Leu | Ser | Gln | Ala 490 | Leu | Lys | Ile | Ile | Met 495 | Asn | Ala | Phe | |
| TAT | GGC | GTG | CTC | GGC | ACC | ACC | GCC | TGC | CGC | TTC | TTC | GAT | CCG | CGG | CTG | 1652 |
| Tyr 500 | Gly | Val | Leu | Gly | Thr 505 | Thr | Ala | Cys | Arg | Phe 510 | Phe | Asp | Pro | Arg | Leu 515 | |
| GCA | TCG | TCG | ATC | ACC | ATG | CGT | GGT | CAT | CAG | ATC | ATG | CGG | CAA | ACC | AAA | 1700 |
| Ala | Ser | Ser | Ile | Thr 520 | Met | Arg | Gly | His | Gln 525 | Ile | Met | Arg | Gln | Thr 530 | Lys | |
| GCG | TTG | ATT | GAA | GCA | CAG | GGC | TAC | GAC | GTT | ATC | TAC | GGC | GAT | ACC | GAC | 1748 |
| Ala | Leu | Ile | Glu 535 | Ala | Gln | Gly | Tyr | Asp 540 | Val | Ile | Tyr | Gly | Asp 545 | Thr | Asp | |
| TCA | ACG | TTT | GTC | TGG | CTG | AAA | GGC | GCA | CAT | TCG | GAA | GAA | GAA | GCG | GCG | 1796 |
| Ser | Thr | Phe 550 | Val | Trp | Leu | Lys | Gly 555 | Ala | His | Ser | Glu | Glu 560 | Glu | Ala | Ala | |
| AAA | ATC | GGT | CGT | GCA | CTG | GTG | CAG | CAC | GTT | AAC | GCC | TGG | TGG | GCG | GAA | 1844 |
| Lys | Ile 565 | Gly | Arg | Ala | Leu | Val 570 | Gln | His | Val | Asn | Ala 575 | Trp | Trp | Ala | Glu | |
| ACG | CTG | CAA | AAA | CAA | CGG | CTG | ACC | AGC | GCA | TTA | GAA | CTG | GAG | TAT | GAA | 1892 |
| Thr 580 | Leu | Gln | Lys | Gln | Arg 585 | Leu | Thr | Ser | Ala | Leu 590 | Glu | Leu | Glu | Tyr | Glu 595 | |
| ACC | CAT | TTC | TGC | CGT | TTT | CTG | ATG | CCA | ACC | ATT | CGC | GGA | GCC | GAT | ACC | 1940 |
| Thr | His | Phe | Cys | Arg 600 | Phe | Leu | Met | Pro | Thr 605 | Ile | Arg | Gly | Ala | Asp 610 | Thr | |
| GGC | AGT | AAA | AAG | CGT | TAT | GCC | GGA | CTG | ATT | CAG | GAG | GGC | GAC | AAG | CAG | 1988 |
| Gly | Ser | Lys | Lys 615 | Arg | Tyr | Ala | Gly | Leu 620 | Ile | Gln | Glu | Gly | Asp 625 | Lys | Gln | |
| CGG | ATG | GTG | TTT | AAA | GGG | CTG | GAA | ACC | GTG | CGC | ACC | GAC | TGG | ACG | CCG | 2036 |
| Arg | Met | Val | Phe 630 | Lys | Gly | Leu | Glu | Thr 635 | Val | Arg | Thr | Asp | Trp 640 | Thr | Pro | |
| CTG | GCC | CAG | CAG | TTT | CAG | CAG | GAG | CTA | TAC | CTG | CGC | ATC | TTC | CGC | AAC | 2084 |
| Leu | Ala | Gln | Gln | Phe 645 | Gln | Gln | Glu | Leu | Tyr 650 | Leu | Arg | Ile | Phe | Arg 655 | Asn | |
| GAG | CCA | TAT | CAG | GAA | TAT | GTA | CGC | GAA | ACC | ATC | GAC | AAA | CTG | ATG | GCG | 2132 |
| Glu | Pro | Tyr | Gln | Glu 660 | Tyr | Val | Arg | Glu | Thr 665 | Ile | Asp | Lys | Leu | Met 670 | Ala 675 | |

| | | | | | | | | | | | | | | | | |
|---|---|---|---|---|---|---|---|---|---|---|---|---|---|---|---|---|
| GGT | GAA | CTG | GAT | GCG | CGA | CTG | GTT | TAC | CGT | AAA | CGC | CTT | CGC | CGT | CCG | 2180 |
| Gly | Glu | Leu | Asp | Ala | Arg | Leu | Val | Tyr | Arg | Lys | Arg | Leu | Arg | Arg | Pro | |
| | | | 680 | | | | | 685 | | | | | | 690 | | |
| CTG | AGC | GAG | TAT | CAG | CGT | AAT | GTG | CCG | CCT | CAT | GTA | CGC | GCC | GCT | CGC | 2228 |
| Leu | Ser | Glu | Tyr | Gln | Arg | Asn | Val | Pro | Pro | His | Val | Arg | Ala | Ala | Arg | |
| | | | 695 | | | | | 700 | | | | | 705 | | | |
| CTT | GCC | GAT | GAA | GAA | AAC | CAA | AAG | CGT | GGT | CGC | CCC | TTG | CAA | TAT | CAG | 2276 |
| Leu | Ala | Asp | Glu | Glu | Asn | Gln | Lys | Arg | Gly | Arg | Pro | Leu | Gln | Tyr | Gln | |
| | | 710 | | | | | 715 | | | | | 720 | | | | |
| AAT | CGC | GGC | ACC | ATT | AAG | TAC | GTA | TGG | ACC | ACC | AAC | GGC | CCG | GAG | CCG | 2324 |
| Asn | Arg | Gly | Thr | Ile | Lys | Tyr | Val | Trp | Thr | Thr | Asn | Gly | Pro | Glu | Pro | |
| | 725 | | | | | 730 | | | | | 735 | | | | | |
| CTG | GAC | TAC | CAA | CGT | TCA | CCA | CTG | GAT | TAC | GAA | CAC | TAT | CTG | ACC | CGC | 2372 |
| Leu | Asp | Tyr | Gln | Arg | Ser | Pro | Leu | Asp | Tyr | Glu | His | Tyr | Leu | Thr | Arg | |
| 740 | | | | | 745 | | | | | 750 | | | | | 755 | |
| CAG | CTA | CAA | CCC | GTG | GCG | GAG | GGA | ATA | CTC | CCT | TTT | ATT | GAG | GAT | AAT | 2420 |
| Gln | Leu | Gln | Pro | Val | Ala | Glu | Gly | Ile | Leu | Pro | Phe | Ile | Glu | Asp | Asn | |
| | | | | 760 | | | | | 765 | | | | | 770 | | |
| TTT | GCT | ACA | CTT | ATG | ACC | GGG | CAA | CTT | GGG | CTA | TTT | TGA | | | | 2459 |
| Phe | Ala | Thr | Leu | Met | Thr | Gly | Gln | Leu | Gly | Leu | Phe | | | | | |
| | | | 775 | | | | | 780 | | | | | | | | |

( 2 ) INFORMATION FOR SEQ ID NO:6:

( i ) SEQUENCE CHARACTERISTICS:
        ( A ) LENGTH: 783 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Val | Ala | Gln | Ala | Gly | Phe | Ile | Leu | Thr | Arg | His | Trp | Arg | Asp | Thr | Pro |
| 1 | | | | 5 | | | | | 10 | | | | | 15 | |
| Gln | Gly | Thr | Glu | Val | Ser | Phe | Trp | Leu | Ala | Thr | Asp | Asn | Gly | Pro | Leu |
| | | | 20 | | | | | 25 | | | | | 30 | | |
| Gln | Val | Thr | Leu | Ala | Pro | Gln | Glu | Ser | Val | Ala | Phe | Ile | Pro | Ala | Asp |
| | | 35 | | | | | 40 | | | | | 45 | | | |
| Gln | Val | Pro | Arg | Ala | Gln | His | Ile | Leu | Gln | Gly | Glu | Gln | Gly | Phe | Arg |
| | 50 | | | | | 55 | | | | | 60 | | | | |
| Leu | Thr | Pro | Leu | Ala | Leu | Lys | Asp | Phe | His | Arg | Gln | Pro | Val | Tyr | Gly |
| 65 | | | | | 70 | | | | | 75 | | | | | 80 |
| Leu | Tyr | Cys | Arg | Ala | His | Arg | Gln | Leu | Met | Asn | Tyr | Glu | Lys | Arg | Leu |
| | | | | 85 | | | | | 90 | | | | | 95 | |
| Arg | Glu | Gly | Gly | Val | Thr | Val | Tyr | Glu | Ala | Asp | Val | Arg | Pro | Pro | Glu |
| | | | 100 | | | | | 105 | | | | | 110 | | |
| Arg | Tyr | Leu | Met | Glu | Arg | Phe | Ile | Thr | Ser | Pro | Val | Trp | Val | Glu | Gly |
| | | 115 | | | | | 120 | | | | | 125 | | | |
| Asp | Met | His | Asn | Gly | Thr | Ile | Val | Asn | Ala | Arg | Leu | Lys | Pro | His | Pro |
| | 130 | | | | | 135 | | | | | 140 | | | | |
| Asp | Tyr | Arg | Pro | Pro | Leu | Lys | Trp | Val | Ser | Ile | Asp | Ile | Glu | Thr | Thr |
| 145 | | | | | 150 | | | | | 155 | | | | | 160 |
| Arg | His | Gly | Glu | Leu | Tyr | Cys | Ile | Gly | Leu | Glu | Gly | Cys | Gly | Gln | Arg |
| | | | | 165 | | | | | 170 | | | | | 175 | |
| Ile | Val | Tyr | Met | Leu | Gly | Pro | Glu | Asn | Gly | Asp | Ala | Ser | Ser | Leu | Asp |
| | | | 180 | | | | | 185 | | | | | 190 | | |
| Phe | Glu | Leu | Glu | Tyr | Val | Ala | Ser | Arg | Pro | Gln | Leu | Leu | Glu | Lys | Leu |
| | | 195 | | | | | 200 | | | | | 205 | | | |

```
Asn  Ala  Trp  Phe  Ala  Asn  Tyr  Asp  Pro  Asp  Val  Ile  Ile  Gly  Trp  Asn
     210            215                 220

Val  Val  Gln  Phe  Asp  Leu  Arg  Met  Leu  Gln  Lys  His  Ala  Glu  Arg  Tyr
225            230                 235                                    240

Arg  Leu  Pro  Leu  Arg  Leu  Gly  Arg  Asp  Asn  Ser  Glu  Leu  Glu  Trp  Arg
               245                      250                           255

Asp  Asp  Gly  Phe  Lys  Asn  Gly  Val  Phe  Phe  Ala  Gln  Ala  Lys  Gly  Gly
               260                 265                      270

Leu  Ile  Ile  Asp  Gly  Ile  Glu  Ala  Leu  Lys  Ser  Ala  Phe  Trp  Asn  Phe
          275                 280                      285

Ser  Ser  Phe  Ser  Leu  Glu  Thr  Val  Ala  Gln  Glu  Leu  Leu  Gly  Glu  Gly
     290                 295                           300

Lys  Ser  Ile  Asp  Asn  Pro  Trp  Asp  Arg  Met  Asp  Glu  Ile  Asp  Arg  Arg
305                      310                 315                           320

Phe  Ala  Glu  Asp  Lys  Pro  Ala  Leu  Ala  Thr  Tyr  Asn  Leu  Lys  Asp  Cys
335                 325                      330                      335

Glu  Leu  Val  Thr  Gln  Ile  Phe  His  Lys  Thr  Glu  Ile  Met  Pro  Phe  Leu
               340                 345                           350

Leu  Glu  Arg  Ala  Thr  Val  Asn  Gly  Leu  Pro  Val  Asp  Arg  His  Gly  Gly
          355                      360                      365

Ser  Val  Ala  Ala  Phe  Gly  His  Leu  Tyr  Phe  Pro  Arg  Met  His  Arg  Ala
     370                 375                      380

Gly  Tyr  Val  Ala  Pro  Asn  Leu  Gly  Glu  Val  Pro  Pro  His  Ala  Ser  Pro
385                      390                 395                           400

Gly  Gly  Tyr  Val  Met  Asp  Ser  Arg  Pro  Gly  Leu  Tyr  Asp  Ser  Val  Leu
               405                      410                      415

Val  Leu  Asp  Tyr  Lys  Ser  Leu  Tyr  Pro  Ser  Ile  Ile  Arg  Thr  Phe  Leu
               420                 425                      430

Ile  Asp  Pro  Val  Gly  Leu  Val  Glu  Gly  Met  Ala  Gln  Pro  Asp  Pro  Glu
          435                 440                      445

His  Ser  Thr  Glu  Gly  Phe  Leu  Asp  Ala  Trp  Phe  Ser  Arg  Glu  Lys  His
     450                 455                      460

Cys  Leu  Pro  Glu  Ile  Val  Thr  Asn  Ile  Trp  His  Gly  Arg  Asp  Glu  Ala
465                      470                 475                           480

Lys  Arg  Gln  Gly  Asn  Lys  Pro  Leu  Ser  Gln  Ala  Leu  Lys  Ile  Ile  Met
               485                      490                      495

Asn  Ala  Phe  Tyr  Gly  Val  Leu  Gly  Thr  Ala  Cys  Arg  Phe  Phe  Asp
               500                 505                      510

Pro  Arg  Leu  Ala  Ser  Ser  Ile  Thr  Met  Arg  Gly  His  Gln  Ile  Met  Arg
          515                 520                      525

Gln  Thr  Lys  Ala  Leu  Ile  Glu  Ala  Gln  Gly  Tyr  Asp  Val  Ile  Tyr  Gly
     530                 535                      540

Asp  Thr  Asp  Ser  Thr  Phe  Val  Trp  Leu  Lys  Gly  Ala  His  Ser  Glu  Glu
545                      550                 555                           560

Glu  Ala  Ala  Lys  Ile  Gly  Arg  Ala  Leu  Val  Gln  His  Val  Asn  Ala  Trp
                    565                 570                      575

Trp  Ala  Glu  Thr  Leu  Gln  Lys  Gln  Arg  Leu  Thr  Ser  Ala  Leu  Glu  Leu
               580                      585                      590

Glu  Tyr  Glu  Thr  His  Phe  Cys  Arg  Phe  Leu  Met  Pro  Thr  Ile  Arg  Gly
          595                 600                      605

Ala  Asp  Thr  Gly  Ser  Lys  Lys  Arg  Tyr  Ala  Gly  Leu  Ile  Gln  Glu  Gly
     610                 615                      620

Asp  Lys  Gln  Arg  Met  Val  Phe  Lys  Gly  Leu  Glu  Thr  Val  Arg  Thr  Asp
625                      630                 635                           640
```

| | | | | | | | | | | | | | | | |
|---|---|---|---|---|---|---|---|---|---|---|---|---|---|---|---|
| Trp | Thr | Pro | Leu | Ala 645 | Gln | Gln | Phe | Gln | Gln 650 | Glu | Leu | Tyr | Leu | Arg 655 | Ile |
| Phe | Arg | Asn | Glu 660 | Pro | Tyr | Gln | Glu | Tyr 665 | Val | Arg | Glu | Thr | Ile 670 | Asp | Lys |
| Leu | Met | Ala 675 | Gly | Glu | Leu | Asp | Ala 680 | Arg | Leu | Val | Tyr | Arg 685 | Lys | Arg | Leu |
| Arg | Arg 690 | Pro | Leu | Ser | Glu | Tyr 695 | Gln | Arg | Asn | Val | Pro 700 | Pro | His | Val | Arg |
| Ala 705 | Ala | Arg | Leu | Ala | Asp 710 | Glu | Glu | Asn | Gln | Lys 715 | Arg | Gly | Arg | Pro | Leu 720 |
| Gln | Tyr | Gln | Asn | Arg 725 | Gly | Thr | Ile | Lys | Tyr 730 | Val | Trp | Thr | Thr | Asn 735 | Gly |
| Pro | Glu | Pro | Leu 740 | Asp | Tyr | Gln | Arg | Ser 745 | Pro | Leu | Asp | Tyr | Glu 750 | His | Tyr |
| Leu | Thr | Arg 755 | Gln | Leu | Gln | Pro | Val 760 | Ala | Glu | Gly | Ile | Leu 765 | Pro | Phe | Ile |
| Glu | Asp 770 | Asn | Phe | Ala | Thr | Leu 775 | Met | Thr | Gly | Gln | Leu 780 | Gly | Leu | Phe | |